United States Patent
Dachs, II et al.

(10) Patent No.: US 10,631,939 B2
(45) Date of Patent: Apr. 28, 2020

(54) SYSTEMS AND METHODS FOR MAPPING FLUX SUPPLY PATHS

(71) Applicant: INTUITIVE SURGICAL OPERATIONS, INC., Sunnyvale, CA (US)

(72) Inventors: Gregory W. Dachs, II, San Mateo, CA (US); Bruce M. Schena, Menlo Park, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 14/070,118

(22) Filed: Nov. 1, 2013

(65) Prior Publication Data

US 2014/0128885 A1    May 8, 2014

Related U.S. Application Data

(60) Provisional application No. 61/721,863, filed on Nov. 2, 2012.

(51) Int. Cl.
*A61B 34/30* (2016.01)
*A61B 18/12* (2006.01)
(Continued)

(52) U.S. Cl.
CPC .......... *A61B 34/30* (2016.02); *A61B 18/1206* (2013.01); *A61B 34/37* (2016.02);
(Continued)

(58) Field of Classification Search
CPC .......... A61B 2018/00172; A61B 2018/00178; A61B 2017/00477; A61B 2017/00482
See application file for complete search history.

(56) References Cited

U.S. PATENT DOCUMENTS 2,175,768 A    10/1939    Anthony
2,249,618 A    7/1941    Perkins
(Continued)

FOREIGN PATENT DOCUMENTS

CN    1243690 A    2/2000
CN    101023886 A    8/2007
(Continued)

OTHER PUBLICATIONS

Applied Surgical, Data Sheet for Gemini Operating Room, 1 Page, 2006; Internet: http://appliedsurgicalsolutions.com/.
(Continued)

*Primary Examiner* — Michael F Peffley
*Assistant Examiner* — Bo Ouyang
(74) *Attorney, Agent, or Firm* — Jones Robb, PLLC

(57) ABSTRACT

A method of supplying flux may include receiving first data at a control system identifying which of a plurality of remotely-controllable kinematic flux delivery structures is operationally coupled to which of a plurality of flux supply pathways and receiving second data at the control system identifying which of the remotely-controllable kinematic flux delivery structures is operationally coupled to which of a plurality of kinematic support structures. A system for supplying flux may include a plurality of flux supply pathways, a plurality of remotely-controllable kinematic flux delivery structures, and a control system receiving first data identifying which of the remotely-controllable kinematic flux delivery structures is operationally coupled to which of the flux supply pathways and receiving second data identifying which of the remotely-controllable kinematic flux delivery structures is operationally coupled to which of a plurality of kinematic support structures.

21 Claims, 13 Drawing Sheets

(51) Int. Cl.
*A61B 34/37* (2016.01)
*A61B 90/98* (2016.01)
A61B 18/00 (2006.01)
A61B 18/14 (2006.01)

(52) U.S. Cl.
CPC .......... *A61B 90/98* (2016.02); *A61B 18/1445* (2013.01); *A61B 2018/00178* (2013.01)

(56) References Cited

U.S. PATENT DOCUMENTS

| | | | |
|---|---|---|---|
| 3,184,703 | A | 5/1965 | Piscitello et al. |
| 4,211,461 | A | 7/1980 | Wescott |
| 4,284,312 | A | 8/1981 | Patchett et al. |
| 5,180,316 | A | 1/1993 | Miller et al. |
| 5,350,314 | A | 9/1994 | Saba |
| 5,991,355 | A | 11/1999 | Dahlke |
| 6,040,537 | A | 3/2000 | McClintock |
| 6,074,388 | A | 6/2000 | Tockweiler et al. |
| 6,113,596 | A | 9/2000 | Hooven et al. |
| 6,237,604 | B1 | 5/2001 | Burnside et al. |
| 6,493,608 | B1 | 12/2002 | Niemeyer |
| 6,522,906 | B1 | 2/2003 | Salisbury, Jr. et al. |
| 6,602,185 | B1 | 8/2003 | Uchikubo |
| 6,702,617 | B1 | 3/2004 | Clement et al. |
| 6,840,938 | B1 | 1/2005 | Morley et al. |
| 6,849,071 | B2 | 2/2005 | Whitman et al. |
| 6,994,708 | B2 | 2/2006 | Manzo |
| 6,997,723 | B2 | 2/2006 | Lee |
| D517,501 | S | 3/2006 | Kotyk |
| 7,122,032 | B2 * | 10/2006 | Shinmura .............. A61B 19/52 128/898 |
| 7,217,269 | B2 | 5/2007 | El-Galley et al. |
| 7,320,700 | B2 | 1/2008 | Cooper et al. |
| 7,353,068 | B2 | 4/2008 | Tanaka et al. |
| 7,367,973 | B2 | 5/2008 | Scott et al. |
| 7,379,563 | B2 | 5/2008 | Shamaie |
| 7,428,439 | B1 | 9/2008 | Reynolds et al. |
| 7,594,912 | B2 | 9/2009 | Cooper et al. |
| 8,052,470 | B1 | 11/2011 | Lin |
| 8,083,548 | B1 | 12/2011 | Lin |
| 8,120,301 | B2 | 2/2012 | Goldberg et al. |
| 8,398,541 | B2 | 3/2013 | Dimaio et al. |
| 8,398,634 | B2 | 3/2013 | Scott et al. |
| 8,418,073 | B2 | 4/2013 | Mohr et al. |
| 8,423,182 | B2 | 4/2013 | Robinson et al. |
| 8,508,173 | B2 | 8/2013 | Goldberg et al. |
| 8,657,808 | B2 | 2/2014 | McPherson et al. |
| 8,862,268 | B2 | 10/2014 | Robinson et al. |
| 9,259,283 | B2 | 2/2016 | Ogawa et al. |
| 9,301,811 | B2 | 4/2016 | Goldberg et al. |
| 9,375,288 | B2 | 6/2016 | Robinson et al. |
| 9,814,536 | B2 | 11/2017 | Goldberg et al. |
| 9,827,059 | B2 | 11/2017 | Robinson et al. |
| 10,092,344 | B2 | 10/2018 | Mohr et al. |
| 2002/0049004 | A1 | 4/2002 | Davis et al. |
| 2002/0152015 | A1 | 10/2002 | Seto |
| 2002/0173799 | A1 | 11/2002 | Besharim et al. |
| 2003/0040204 | A1 | 2/2003 | Chen et al. |
| 2003/0135204 | A1 | 7/2003 | Lee et al. |
| 2004/0152354 | A1 | 8/2004 | Luther et al. |
| 2004/0167515 | A1 | 8/2004 | Petersen et al. |
| 2004/0169673 | A1 | 9/2004 | Crampe et al. |
| 2005/0008043 | A1 | 1/2005 | Kousek et al. |
| 2005/0021021 | A1 | 1/2005 | Foltz et al. |
| 2005/0080403 | A1 | 4/2005 | Takahashi |
| 2005/0251156 | A1 | 11/2005 | Toth et al. |
| 2005/0251228 | A1 | 11/2005 | Hamel |
| 2006/0079889 | A1 | 4/2006 | Manzo |
| 2006/0087746 | A1 | 4/2006 | Lipow |
| 2006/0142657 | A1 | 6/2006 | Quaid et al. |
| 2006/0167440 | A1 | 7/2006 | Cooper et al. |
| 2006/0178559 | A1 | 8/2006 | Kumar et al. |
| 2006/0271260 | A1 | 11/2006 | Matsuzaki et al. |
| 2007/0005045 | A1 | 1/2007 | Mintz et al. |
| 2007/0013336 | A1 | 1/2007 | Nowlin et al. |
| 2007/0016174 | A1 | 1/2007 | Millman et al. |
| 2007/0078539 | A1 | 4/2007 | Kuhner et al. |
| 2007/0167968 | A1 | 7/2007 | Pandey |
| 2007/0239172 | A1 | 10/2007 | Lee et al. |
| 2008/0004603 | A1 | 1/2008 | Larkin et al. |
| 2008/0020714 | A1 | 1/2008 | Mezhinsky et al. |
| 2008/0046122 | A1 | 2/2008 | Manzo et al. |
| 2008/0125794 | A1 | 5/2008 | Brock et al. |
| 2008/0140158 | A1 | 6/2008 | Hamel et al. |
| 2008/0147089 | A1 * | 6/2008 | Loh .................... A61B 1/00149 606/130 |
| 2008/0183189 | A1 | 7/2008 | Teichman et al. |
| 2008/0217564 | A1 | 9/2008 | Beyar et al. |
| 2008/0221473 | A1 | 9/2008 | Calancie et al. |
| 2008/0249547 | A1 | 10/2008 | Dunn |
| 2008/0262538 | A1 | 10/2008 | Danitz et al. |
| 2008/0319313 | A1 | 12/2008 | Boivin et al. |
| 2009/0009492 | A1 | 1/2009 | Gregorio et al. |
| 2009/0012533 | A1 * | 1/2009 | Barbagli ................ A61B 19/22 606/130 |
| 2009/0024142 | A1 | 1/2009 | Ruiz |
| 2009/0088634 | A1 | 4/2009 | Zhao et al. |
| 2009/0088774 | A1 * | 4/2009 | Swarup .............. A61B 19/2203 606/130 |
| 2009/0245600 | A1 | 10/2009 | Hoffman et al. |
| 2009/0248036 | A1 | 10/2009 | Hoffman et al. |
| 2009/0248041 | A1 | 10/2009 | Williams et al. |
| 2009/0254077 | A1 * | 10/2009 | Craig ................ A61B 18/1206 606/33 |
| 2009/0275940 | A1 * | 11/2009 | Malackowski .... A61B 18/1442 606/42 |
| 2010/0082039 | A1 | 4/2010 | Mohr et al. |
| 2010/0191088 | A1 | 7/2010 | Anderson et al. |
| 2010/0228249 | A1 | 9/2010 | Mohr et al. |
| 2010/0228264 | A1 * | 9/2010 | Robinson ........... A61B 18/1206 606/130 |
| 2010/0234857 | A1 | 9/2010 | Itkowitz et al. |
| 2010/0305427 | A1 | 12/2010 | Huber et al. |
| 2011/0045680 | A1 | 2/2011 | Beller et al. |
| 2011/0079626 | A1 | 4/2011 | Viola et al. |
| 2011/0118748 | A1 | 5/2011 | Itkowitz et al. |
| 2011/0118752 | A1 | 5/2011 | Itkowitz et al. |
| 2011/0118753 | A1 | 5/2011 | Itkowitz et al. |
| 2011/0121049 | A1 | 5/2011 | Malinouskas et al. |
| 2011/0238079 | A1 | 9/2011 | Hannaford et al. |
| 2011/0276058 | A1 | 11/2011 | Choi et al. |
| 2011/0282140 | A1 | 11/2011 | Itkowitz et al. |
| 2011/0282141 | A1 | 11/2011 | Itkowitz et al. |
| 2012/0046659 | A1 | 2/2012 | Mueller |
| 2012/0059390 | A1 | 3/2012 | Mintz et al. |
| 2012/0071891 | A1 | 3/2012 | Itkowitz et al. |
| 2012/0071892 | A1 | 3/2012 | Itkowitz et al. |
| 2012/0116381 | A1 * | 5/2012 | Houser ............ A61B 17/00234 606/33 |
| 2012/0180751 | A1 | 7/2012 | Tuerk et al. |
| 2012/0202388 | A1 | 8/2012 | Selig et al. |
| 2012/0232540 | A1 | 9/2012 | Baur et al. |
| 2012/0248167 | A1 | 10/2012 | Flanagan et al. |
| 2012/0310241 | A1 * | 12/2012 | Orszulak ................ A61B 18/12 606/51 |
| 2013/0053840 | A1 | 2/2013 | Krapohl et al. |
| 2013/0231681 | A1 | 9/2013 | Robinson et al. |
| 2013/0274734 | A1 | 10/2013 | Maass et al. |
| 2013/0304256 | A1 | 11/2013 | Moll et al. |
| 2014/0081455 | A1 | 3/2014 | Goldberg et al. |
| 2014/0094968 | A1 | 4/2014 | Taylor et al. |
| 2014/0128886 | A1 | 5/2014 | Holop et al. |
| 2014/0142591 | A1 | 5/2014 | Alvarez et al. |
| 2014/0180272 | A1 | 6/2014 | Dachs, II et al. |
| 2014/0378995 | A1 | 12/2014 | Kumar et al. |
| 2015/0012134 | A1 | 1/2015 | Robinson et al. |
| 2015/0173849 | A1 | 6/2015 | Robinson et al. |
| 2016/0192998 | A1 | 7/2016 | Goldberg et al. |
| 2016/0314710 | A1 | 10/2016 | Jarc et al. |
| 2016/0338786 | A1 | 11/2016 | Robinson et al. |

(56) References Cited

U.S. PATENT DOCUMENTS

| | | | |
|---|---|---|---|
| 2017/0209226 | A1 | 7/2017 | Overmyer et al. |
| 2018/0036087 | A1 | 2/2018 | Goldberg et al. |
| 2018/0049828 | A1 | 2/2018 | Robinson et al. |

FOREIGN PATENT DOCUMENTS

| | | | |
|---|---|---|---|
| CN | 101027010 | A | 8/2007 |
| CN | 101297760 | A | 11/2008 |
| CN | 101902979 | A | 12/2010 |
| CN | 102723645 | A | 10/2012 |
| CN | 102727302 | A | 10/2012 |
| JP | H07308321 | A | 11/1995 |
| JP | 2001314411 | A | 11/2001 |
| JP | 2004208922 | A | 7/2004 |
| JP | 2006255395 | A | 9/2006 |
| JP | 2009544422 | A | 12/2009 |
| JP | 2011506008 | A | 3/2011 |
| JP | 2011104379 | A | 6/2011 |
| JP | 2012169273 | A | 9/2012 |
| WO | WO-9749340 | A1 | 12/1997 |
| WO | WO-2006039092 | A2 | 4/2006 |
| WO | WO-2007075864 | A1 | 7/2007 |
| WO | WO-2008098085 | A2 | 8/2008 |
| WO | WO-2009120940 | A3 | 12/2009 |
| WO | WO-2010008126 | A1 | 1/2010 |
| WO | WO-2010104753 | A1 | 9/2010 |
| WO | WO-2011060139 | A2 | 5/2011 |
| WO | WO-2011125007 | A1 | 10/2011 |

OTHER PUBLICATIONS

Dugan, Kelli M., "Stepping Out," Birmingham Business Journal, Mar. 24, 2006, 2 pages; Internet: http://www.oadi.org/client%20news/Applied%20Surgical%20032406.pdf.
Harris, William, "How Haptic Technology Works," downloaded Oct. 24, 2008, 6 pages; Internet: http://electronics.howstuffworks.com/gadgets/other-gadgets/haptic-technology4.htm.
International Search Report and Written Opinion for Application No. PCT/US2013/059938, dated Dec. 10, 2013, 11 pages.
Linemaster Switch Corp., Brochure titled "Precision Begins with a Linemaster Switch," 8 pages, 2000.
Linemaster Switch Corp., Data Sheet for Linemaster Wireless Linear Foot Switch, Lit-002 Rev D, 2 pages, downloaded Jan. 2, 2009; Internet: http://www.linemaster.com/media/DataSheets/LIT-002%20Rev%20Dsm.pdf.
Linemaster Switch Corp., Information sheet for Linemaster Infrared Wireless Linear Foot Switch, 2 pages, downloaded Jan. 2, 2009; Internet: http://www.linemaster.com/wirelesslinear.shtml.
Medical Design Magazine, "Wireless Footswitch Controls Several Surgical Devices," Nov. 1, 2006, 1 page; Internet: http://medicaldesign.com/engineering-prototyping/wireless_footswitch_controls/index.html.
PCT/US10/26307 International Search Report and Written Opinion of the International Searching Authority, dated Jul. 22, 2010, 9 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Wikipedia, entry on "Ergonomics," printed Feb. 24, 2009 at 11:24 p.m., 10 pages; Internet: http://en.wikipedia.org/wiki/Ergonomics.
Erickson, J.R. et al., "Connectors Take on a new Life," Published Online on Sep. 1, 2012, <URL: http://www.designworlddonline.com/connectors-take-on-a-new-life/>.
International Search Report and Written Opinion for Application No. PCT/US2013/068059, dated Feb. 11, 2014, 18 pages.
802.3af-2003—IEEE Standard for Information Technology—Telecommunications and Information Exchange Between Systems—Local and Metropolitan Area Networks—Specific Requirements [online], 2003, Current Version Jul. 22, 2003, DOI 10.1109/IEEESTD 2003.94284, Persistent Link: http://ieeexplore.ieee.org/servlet/opac?punumber=8612.
PCT/US10/56345 International Search Report and Written Opinion of the International Searching Authority, dated Feb. 8, 2011, 15 pages.
Office Action dated Oct. 8, 2016 for Chinese Application No. 201380048070.8 filed Sep. 16, 2013, 15 pages.
Extended European Search Report for Application No. 13851407.0, dated Sep. 9, 2016, 13 pages.
Extended European Search Report for Application No. 13836661.2, dated Apr. 28, 2016, 11 pages.
Partial Supplementary European Search Report for Application No. 13851407.0, dated May 23, 2016, 9 pages.
Office Action dated May 8, 2017 for Chinese Application No. 201380057047.5 filed Nov. 1, 2013, 14 pages.
Communication dated Mar. 12, 2018, received from the European Patent Office in European Patent Application No. 13851407.0 (6 pages).

\* cited by examiner

SYSTEMS AND METHODS FOR MAPPING FLUX SUPPLY PATHS

This application claims the benefit of U.S. Provisional Application No. 61/721,863, filed Nov. 2, 2012, which is incorporated by reference herein in its entirety.

TECHNICAL FIELD

Aspects of the present disclosure relate to systems and methods for automated detection and mapping of flux supply paths between multiple flux supply sources and multiple remotely-controllable flux delivery structures. More particularly, aspects of the present disclosure relate to systems and methods for determining which of a plurality of electrosurgical instruments installed at patient side cart of a robotic (teleoperated) surgical system is in energy communication with which of a plurality of electrical energy supply sources, and controlling energy supply based on the same.

INTRODUCTION

Some minimally invasive surgical techniques are performed remotely through the use of robotically-controlled (teleoperated) surgical instruments of teleoperated surgical systems. In robotically-controlled (teleoperated) surgical systems, surgeons manipulate input devices at a surgeon console, and those inputs are passed to a patient side cart that interfaces with one or more teleoperated surgical instruments. Based on the surgeon's inputs at the surgeon console, the one or more teleoperated surgical instruments are actuated at the patient side cart to operate on the patient, thereby creating a master-slave control relationship between the surgeon console and the surgical instrument(s) at the patient side cart.

Some surgical instruments are configured for delivery of a flux to a patient. Such instruments can be placed in operational connection with a flux source that generates and supplies flux to the surgical instrument to be delivered to a patient during a surgical procedure.

By way of particular example, electrosurgical instruments can be placed in communication with an electrical energy generator to deliver cautery energy in teleoperated surgical systems to perform a cautery procedure (e.g., tissue ablation, tissue sealing, tissue cutting, etc.). The surgical instruments that delivery cautery energy may include, for example, monopolar instruments or bipolar instruments. Monopolar instruments typically deliver electrical energy through a single source electrode and a return, or sink, electrode that returns electrical energy back to an energy generator disposed externally to the patient. Examples of monopolar electrosurgical instruments include, but are not limited to, hooks, spatulas, shears including two blades energized with the same electric potential, cautery probes, irrigators, scissors, etc. Bipolar instruments typically deliver electrical energy through two electrodes (e.g., source and sink electrodes), typically two jaws of the surgical instrument, separately, and the return path for the current is from one pole through the other pole. Examples of bipolar instruments include, but are not limited to, graspers, forceps, clamps, etc., which are generally used for sealing vessels and vascular tissue, grasping vessels, cauterizing or coagulating tissue, etc. Other types of energy (e.g., ultrasound and/or laser) also may be delivered to the patient through surgical instruments mounted at the patient side cart.

Electrosurgical instruments, and others that deliver flux to the patient, are somewhat unique in that, in addition to being coupled to various actuation interface mechanisms at the patient side cart to control movement of the instrument based on the master inputs, they also are in communication with a flux source, e.g., an electrical energy generator in communication with an electrosurgical instrument. As with the movement of the instrument in general, flux delivery from such a surgical instrument to the patient is responsive to an input (e.g., pressing of a foot pedal or other input device) at the surgeon console.

It may be desirable for various reasons to have more than one surgical instrument configured for flux delivery (e.g., more than one electrosurgical instrument) mounted at the patient side cart during a teleoperated surgical procedure. A need exists, however, to provide a teleoperated surgical system that can reliably and in an automated manner determine which one(s) of a plurality of surgical instruments mounted at a patient side cart is operationally coupled with a specific flux supply source. There also exists a need to provide various control schemes and automated control methods relating to flux delivery to surgical instruments of teleoperated surgical systems. Further, there exists a need to manage flux delivery to such instruments in ambiguous conditions where it may be uncertain which instrument will be activated upon a given input command at the surgeon console.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a method of supplying flux may include receiving first data at a control system identifying which of a plurality of remotely-controllable kinematic flux delivery structures is operationally coupled to which of a plurality of flux supply pathways. The method may also include receiving second data at the control system identifying which of the remotely-controllable kinematic flux delivery structures is operationally coupled to which of a plurality of kinematic support structures. The method may also include, in response to an input command signal to deliver flux from a selected one of the remotely-controllable kinematic flux delivery structures that is received by the control system, sending a signal to supply flux from the flux supply pathway operationally coupled to the selected one of the remotely-controllable kinematic flux delivery structures based on the first data and the second data.

In accordance with another exemplary embodiment, a system for supplying flux may include a plurality of flux supply pathways, a plurality of remotely-controllable kinematic flux delivery structures operationally coupled to the flux supply pathways to receive flux, and a control system configured to receive first data identifying which of the remotely-controllable kinematic flux delivery structures is operationally coupled to which of the flux supply pathways and receive second data identifying which of the remotely-controllable kinematic flux delivery structures is operationally coupled to which of the kinematic support structures. In response to an input command signal to deliver flux from a selected one of the remotely-controllable kinematic flux delivery structures, the control system sends a signal to supply flux from one of the flux supply pathways operationally coupled to one of the remotely-controllable kinematic flux delivery structure based on the first data and the second data.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation. In the drawings.

DETAILED DESCRIPTION

Figure 1:
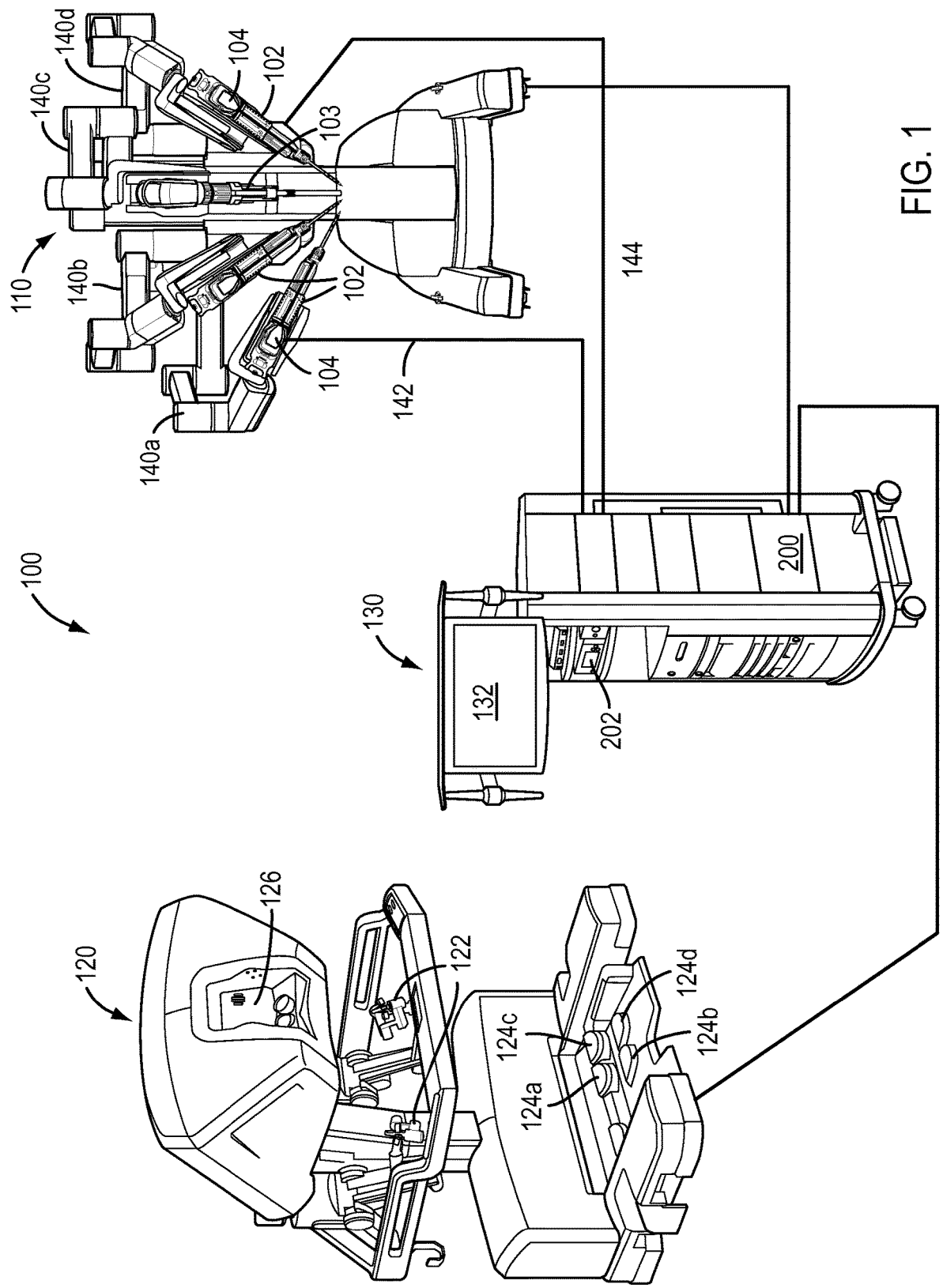
FIG. 1 is a diagrammatic view of an exemplary teleoperated surgical system in accordance with at least one exemplary embodiment.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures, and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Surgical instruments that require connection with a flux source may be connected to such a source by a user, for example, a surgeon's assistant or other operating room personnel. As surgery progresses and instruments are installed and removed from the patient side cart, it may become difficult for the personnel to track and determine which instrument will receive flux from a flux source in response to a given input command at the surgeon console. In some teleoperated surgical systems, if an input device is actuated, flux will be supplied from a particular flux source. If a surgical instrument is operationally coupled to that flux source, flux will be transmitted to the instrument, thereby enabling the instrument to deliver the flux to the patient. However, conventional teleoperated surgical systems are not able to automatically determine which instrument will receive flux upon actuation of a particular input device. Further, if, for example, a plurality of electrosurgical instruments are installed at the patient side cart, conventional surgical systems may prevent two instruments of the same energy type from operating at the same time because some ambiguity may exist as to which instrument will be energized when an energy input command is provided at a surgeon console.

Although for ease of description various exemplary embodiments set forth below describe electrosurgical instruments, electrosurgical energy supply sources, and the delivery of electrosurgical energy (e.g., such as energy for cautery procedures ranging from 100s of volts to 1000s of volts), those having ordinary skill in the art will appreciate that the present disclosure can be applied to a variety of surgical instruments that are provided to deliver various types of flux (e.g., other energy fluxes (such as laser, ultrasound, etc.), a fluid flux, a vacuum pressure flux, smoke evacuation, etc.) by a remotely controlled, external flux generator or other flux supply source to deliver the desired flux to a patient for use in performing, or observing, a surgical procedure. As used herein, the term "flux" may be defined as a flow useful in surgical operations that is transmitted from one source to another source, for example, between a flux supply source and a flux delivery component, such as, for example, an electrosurgical instrument (e.g., to be delivered via end effector thereof).

Nonlimiting examples of types of fluxes encompassed by the present disclosure, with appropriate modification to components using or transmitting the flux may include, for example, electrical energy (e.g., for cautery or nerve stimulation), laser energy, ultrasound energy, or radio frequency energy; fluids (e.g., liquids or gases); image and/or audio streams; vacuum pressure (in which case a negative pressure flux from a vacuum "source" is "delivered" to the instrument), etc. Nonlimiting examples of the flux source may include, for example, energy generators (including, for example, cautery energy and/or nerve stimulation energy generators), fluid delivery sources (e.g., for irrigation), gas supply sources, vacuum sources, etc. By way of nonlimiting example, as will be appreciated by those of ordinary skill in the art, laser energy can be delivered via a fiber optic transmission cable from a laser energy generator to a surgical instrument having an end effector configured to deliver the laser energy to the patient. Further, a flux supply source as used herein can be considered as a sink (e.g., in the case of suction).

Thus, it will be appreciated by one of ordinary skill in the art that the systems and methods described herein with reference to electrosurgical instruments and the delivery of electrical energy are not intended to be limiting and can be used in conjunction with other remotely controlled surgical instruments supplied with remotely delivered fluxes from one or more flux sources. Transmission of the flux from the flux source to the surgical instrument can be via a flux transmission conduit, such as, for example, an electrical energy transmission cable, a hose, a fiber optic cable, etc., configured to be connected to the surgical instrument at one end and to a flux source.

Various exemplary embodiments contemplate a teleoperated surgical system in which a surgical instrument, such as an electrosurgical instrument, is mounted at a patient side cart through an actuation interface assembly. The structure of the instrument in combination with the actuation interface assembly, which is attached to a support structure configured to support the instrument at the patient side cart, may be referred to herein as a remotely-controlled kinematic flux delivery structure. Various exemplary embodiments contemplate a teleoperated surgical system that is able to determine which of a plurality of remotely-controllable kinematic flux delivery structures is operationally coupled to which of a plurality of flux sources in order to determine which of the remotely-controllable kinematic flux delivery structures will be supplied with flux (e.g., energized) when a specific input command is received an input device of a surgeon console. This determination can permit two remotely-controllable kinematic flux delivery structures, including, for example, two electrosurgical instruments of the same energy type to be used at the same time by allowing the system to resolve the ambiguity. Thus, various exemplary embodiments contemplate a way to eliminate potential user errors in correctly tracking which surgical instruments are connected to which flux sources. Various exemplary embodiments contemplate enabling the teleoperated surgical system, based on the above determination and an input command, to supply flux from a particular flux supply source to a specific kinematic flux delivery structure operationally coupled to be actuated in response to the input command.

In accordance with various exemplary embodiments, therefore, because the teleoperated surgical system can determine which of a plurality of surgical instruments installed at an actuation interface assembly are operationally coupled to a specific flux supply source, the system can control the delivery of flux to the various surgical instruments. In particular, because the system is able to associate a specific kinematic structure, which includes a specific surgical instrument at a specific actuation interface assembly to which the instrument is coupled, with a flux supply source, then input devices that provide input commands to supply flux through a flux supply source are able to be unambiguously mapped to the kinematic flux delivery structures.

Various exemplary embodiments also contemplate simplifying the user experience by eliminating the requirement of surgical assistants to manually track which surgical instruments are connected to which flux sources. In addition, various exemplary embodiments contemplate connecting surgical instruments to flux sources using flux transmission conduits that allow the transmission of identification information which identifies the instruments connected with specific flux sources to the teleoperated surgical system.

Teleoperated Surgical System

With reference now to FIG. 1, a (robotic) teleoperated surgical system 100 is provided which, in an exemplary embodiment, performs minimally invasive surgical procedures by interfacing with and controlling a variety of remotely operated surgical instruments, such as one or more electrosurgical instruments 102, as those of ordinary skill in the art are generally familiar. The surgical instruments 102 may be selected from a variety of instruments that are configured to perform various surgical procedures, and in accordance with various exemplary embodiments can be electrosurgical instruments, for example, bipolar and/or monopolar electrosurgical instruments. Some surgical instruments can also be so-called mixed mode, which permit the delivery of both monopolar and bipolar energy.

As illustrated in the schematic view of FIG. 1 the teleoperated surgical system 100 includes a patient side cart 110, a surgeon console 120, and control cart 130. In non-limiting exemplary embodiments of the teleoperated surgical system, the control cart 130 includes "core" processing equipment, such as core processor 200, discussed below, and/or other auxiliary processing equipment, which may be incorporated into or physically supported at the control cart 130. The control cart 130 may also include other controls for operating the teleoperated surgical system. As will be discussed in more detail below, in an exemplary embodiment, signals transmitted from surgeon console 120 may be transmitted to one or more processors at control cart 130, which may interpret the signals and generate commands to be transmitted to the patient side cart 110 to cause manipulation of one or more of electrosurgical instruments and/or patient side manipulators 140a-d to which the electrosurgical instruments are coupled at the patient side cart 110. It is noted that the system components in FIG. 1 are not shown in any particular positioning and can be arranged as desired, with the patient side cart 110 being disposed relative to the patient so as to effect surgery on the patient. A non-limiting, exemplary embodiment of a teleoperated surgical system with which the instruments 102 can be utilized is a da Vinci® Si (model no. IS3000) commercialized by Intuitive Surgical, Inc. of Sunnyvale, Calif.

In general, the surgeon console 120 receives inputs from a user, e.g., a surgeon, by various input devices, including but not limited to, gripping mechanisms 122 and foot pedals 124, etc. and serves as a master controller by which instruments mounted at the patient side cart 110 act as slaves to implement the desired motions of the surgical instrument(s) (e.g., instrument 102), and accordingly perform the desired surgical procedure. For example, while not being limited thereto, the gripping mechanisms 122 may act as "master" devices that may control the electrosurgical instruments 102, which may act as the corresponding "slave" devices at the manipulator arms 140. Further, while not being limited thereto, the foot pedals 124 may be depressed to provide, for example, monopolar or bipolar electrosurgical energy to the instrument 102.

In various exemplary embodiments, suitable output units may include, but are not limited to, a viewer or display 126 that allows the surgeon to view a three-dimensional image of the surgical site, for example, during the surgical procedure, e.g., via an optical endoscope 103 at the patient side cart 110. Other output units may include a speaker (or other component capable of transmitting sound), and/or a component with which a surgeon is in contact that can vibrate or the like to provide haptic feedback. In various exemplary embodiments, the one or more output units may be part of the surgeon console 120 and signals can be transmitted from the control cart 130 thereto. Although in various exemplary embodiments, one or more input mechanisms 122, 124 may be integrated into the surgeon console 120, various other input mechanisms may be added separately and provided so as to be accessible to the surgeon during use of the system, but not necessarily integrated into the surgeon console 120. In the context of the present disclosure, such additional input mechanisms are considered part of the surgeon console.

Thus, a "surgeon console" as used herein includes a console that comprises one or more input devices 122, 124a-d that a surgeon can manipulate to transmit signals, generally through a control cart such as 130 described in more detail below, to actuate a remotely-controllable kinematic structure (e.g., surgical instruments 102 mounted at arms 140) at the patient side cart 110. The surgeon console 120 may also include one or more output devices that can provide feedback to the surgeon. As used herein, it should be understood, however, that a surgeon console can include a unit (e.g., substantially as shown by element 120 in FIG. 1) that integrates the various input and output devices, with, for example, a display, but also can include separate input and/or output devices that are in signal communication with the controllers, such as controllers provided at the control cart and accessible by a surgeon, although not necessarily integrated within a unit with various other input devices. As an example, input units may be provided directly at the control cart 130 and may provide input signals to a processor at the control cart. As such, a "surgeon console" does not necessarily require all of the input and output devices to be integrated into a single unit and can include one or more separate input and/or output devices.

Figure 6:
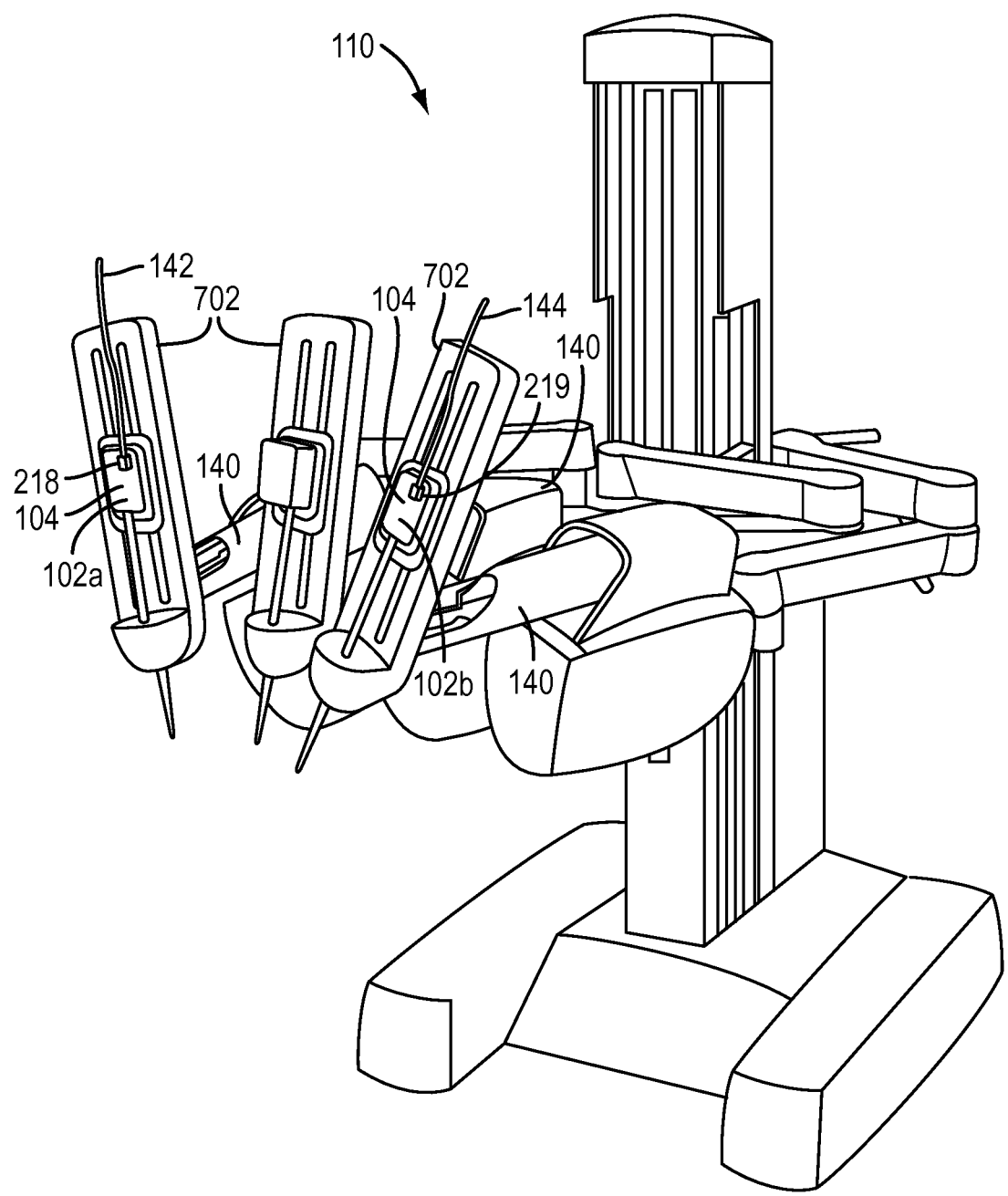
FIG. 6 is a perspective view of an exemplary embodiment of a patient side cart.
Figure 7:
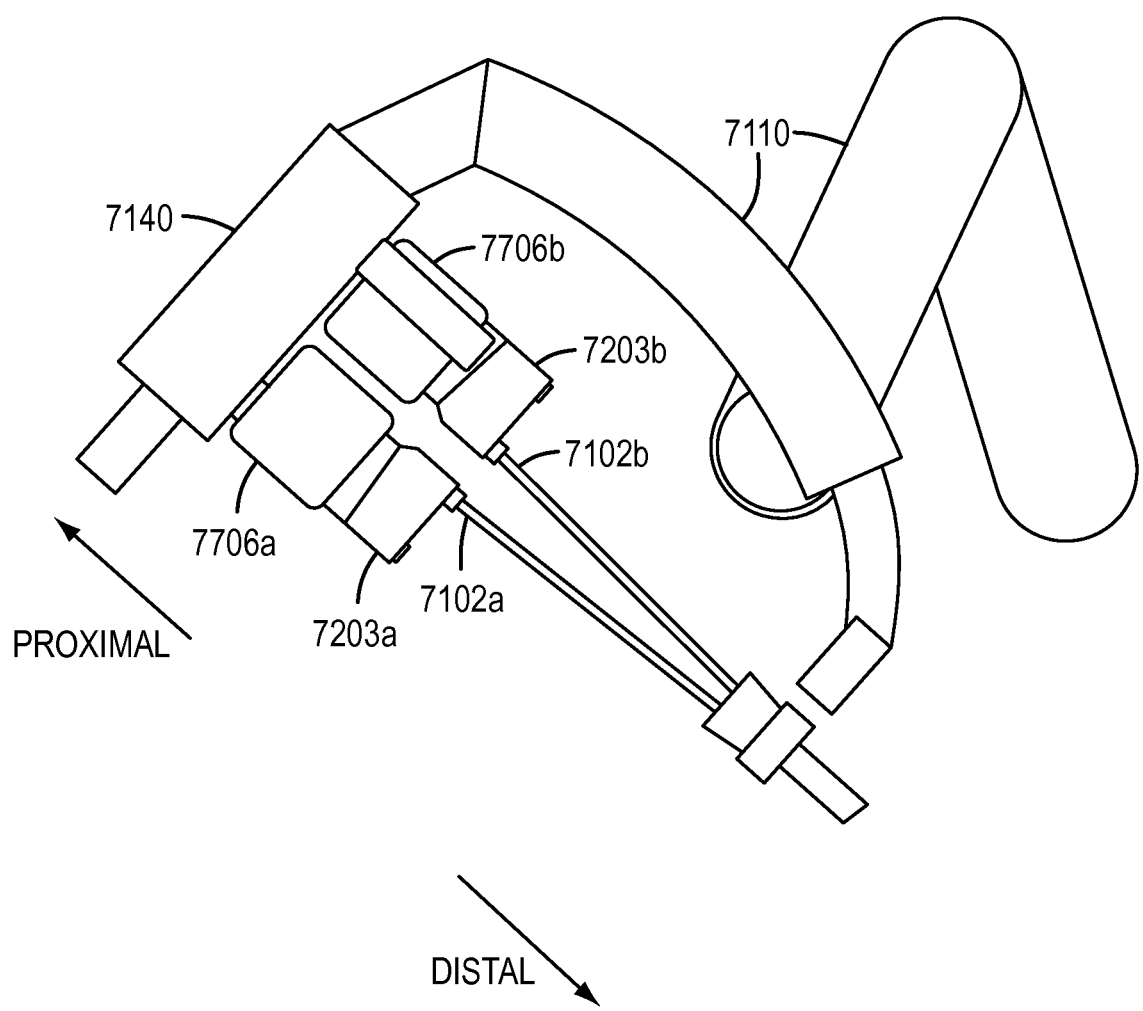
FIG. 7 is a partial schematic view of an exemplary embodiment of a manipulator arm of a patient side cart with two electrosurgical instruments in an installed position, one of which is shown in electrical communication with a flux generator.

The exemplary embodiments of FIG. 1 and FIG. 6, illustrate a patient side cart 110, with multiple, independently moveable manipulator arms 140 that can support an actuation interface assembly (such as, e.g., 700 shown in FIG. 8) and are configured to hold and manipulate various tools, including, but not limited to, for example, a surgical instrument (e.g., electrosurgical instruments 102), and an endoscope 103. However, those having ordinary skill in the art will appreciate that other patient side cart configurations may be used, such as in the embodiment of FIG. 7. In FIG. 7, a patient side cart may have a single manipulator arm 7110 or single support structure that can support plural surgical instrument actuation interface assemblies 7706a, 7706b mounted on a common base 7140. The actuation interface assemblies interface with transmission mechanisms housed in transmission housings 7203a, 7203b of multiple surgical instruments 7102a, 7102b.

Based on the commands input to input devices at, for example, the surgeon console 120, the patient side cart 110 can position and actuate the instrument(s) 102, 7102 to perform a desired medical procedure via the actuation interface assemblies 706, 7706 at the manipulator arm 140, 7140. The actuation interface assemblies 706, 7706 are configured to engage with transmission mechanisms 104, 7203 provided at a proximal end of the surgical instruments 102 (the "proximal" and "distal" directions being shown in FIGS. 7 and 8 relative to the surgical instrument). The electrosurgical instrument 102 and the actuation interface assembly 706 may be mechanically and electrically connected to be able to operate the instrument 102. According to at least one exemplary embodiment, a drape 704 (shown in FIG. 8) may be provided between the patient side cart 110, particularly over the manipulator arms 140, and the surgical instrument 102 in order to create a sterile boundary between the sterile field, which may include a sterile adapter 700 of the actuation interface assembly 706 to which a sterile surgical instrument 102, 7102 is attached, and the non-sterile patient side cart 110.

A control system receives and transmits various control signals to and from the patient side cart 110 and the surgeon console 120, and can transmit light and process images (e.g., from an endoscope at the patient side cart 110) for display, such as, e.g., display 126 at the surgeon console 120 and/or on a display 132 associated with the control cart 130.

Figure 2:
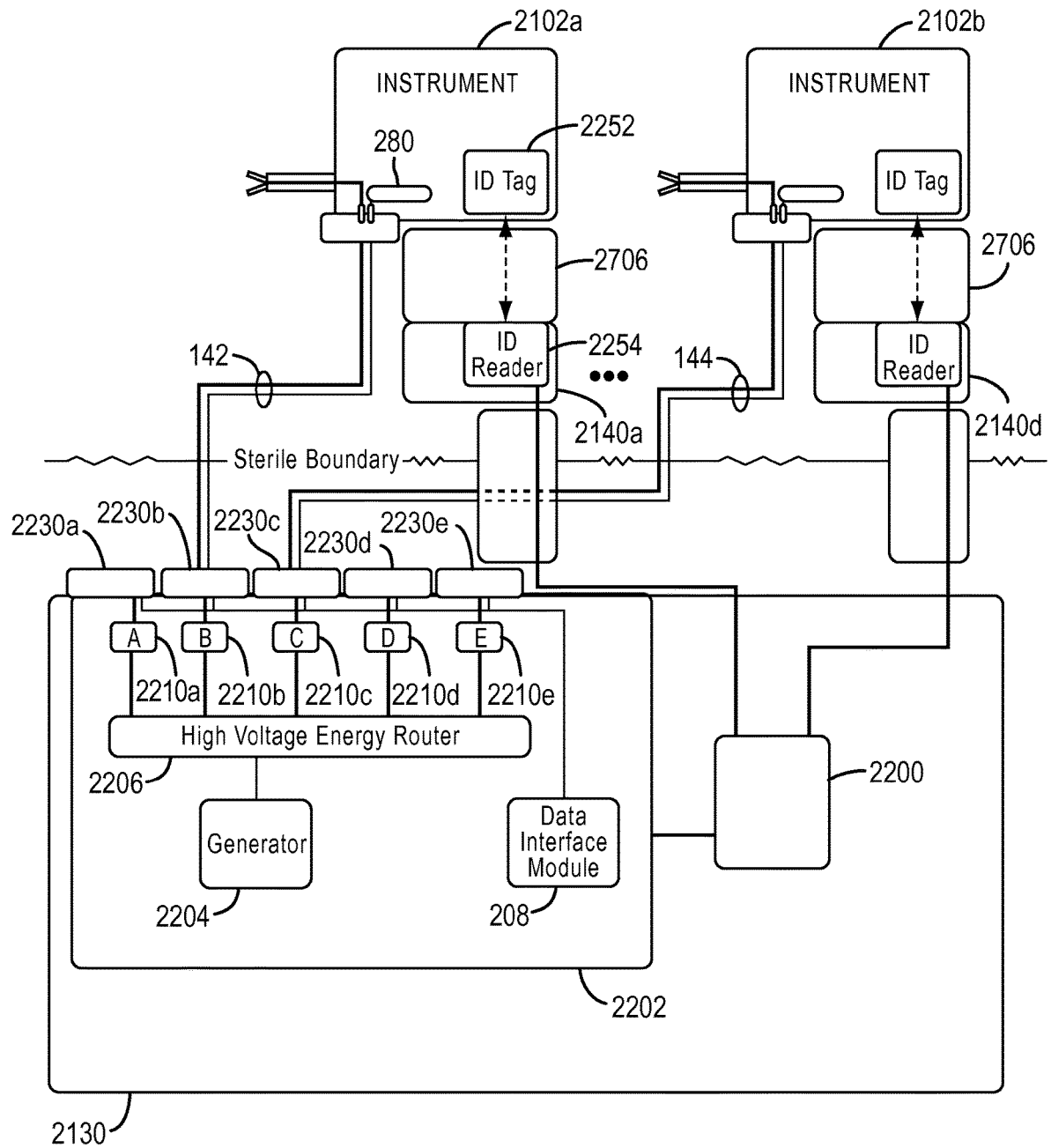
FIG. 2 is a schematic block diagram of an exemplary teleoperated surgical system in accordance with at least one exemplary embodiment.
Figure 3:
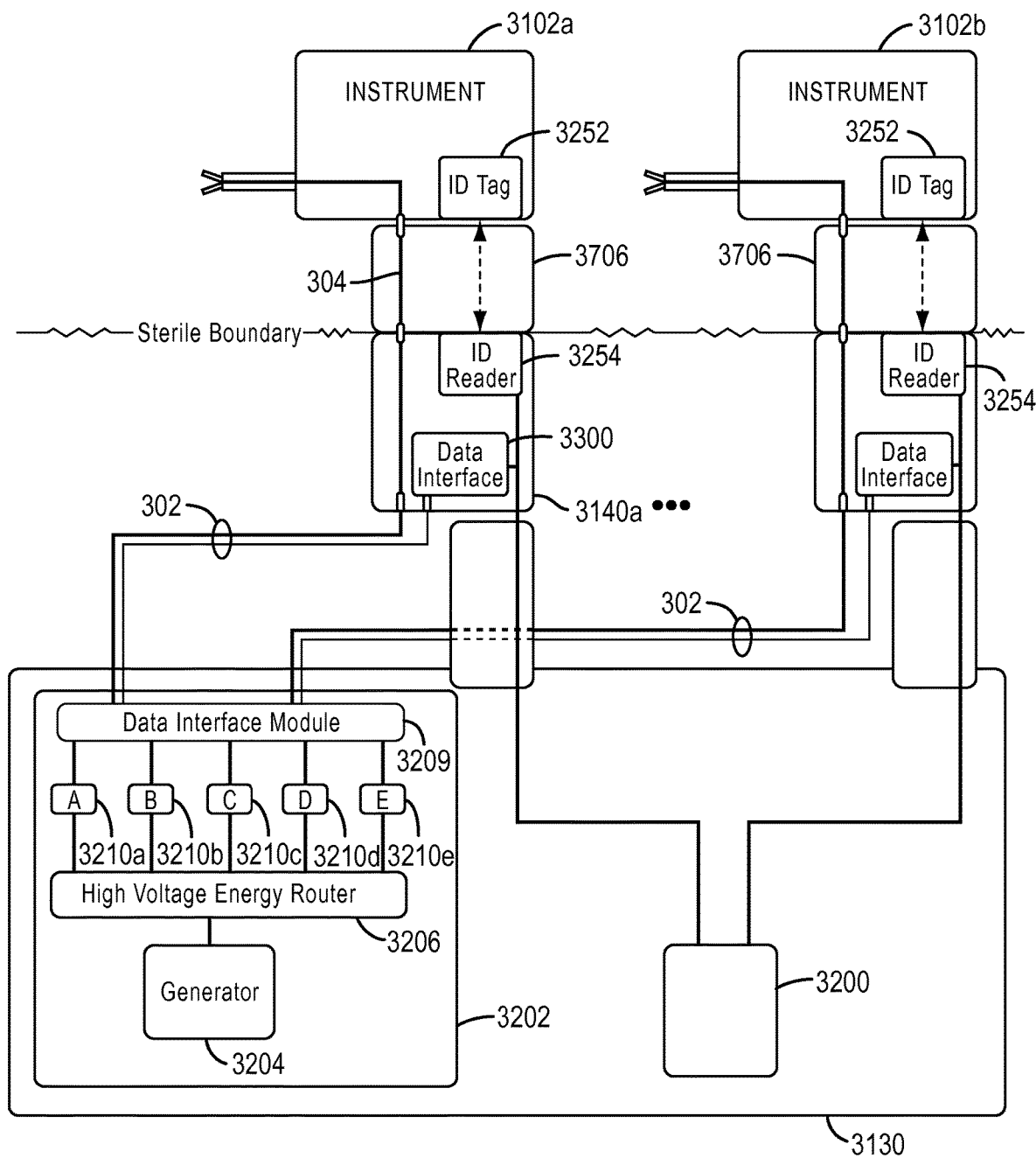
FIG. 3 is a schematic block diagram of an exemplary teleoperated surgical system in accordance with at least one exemplary embodiment.
Figure 4:
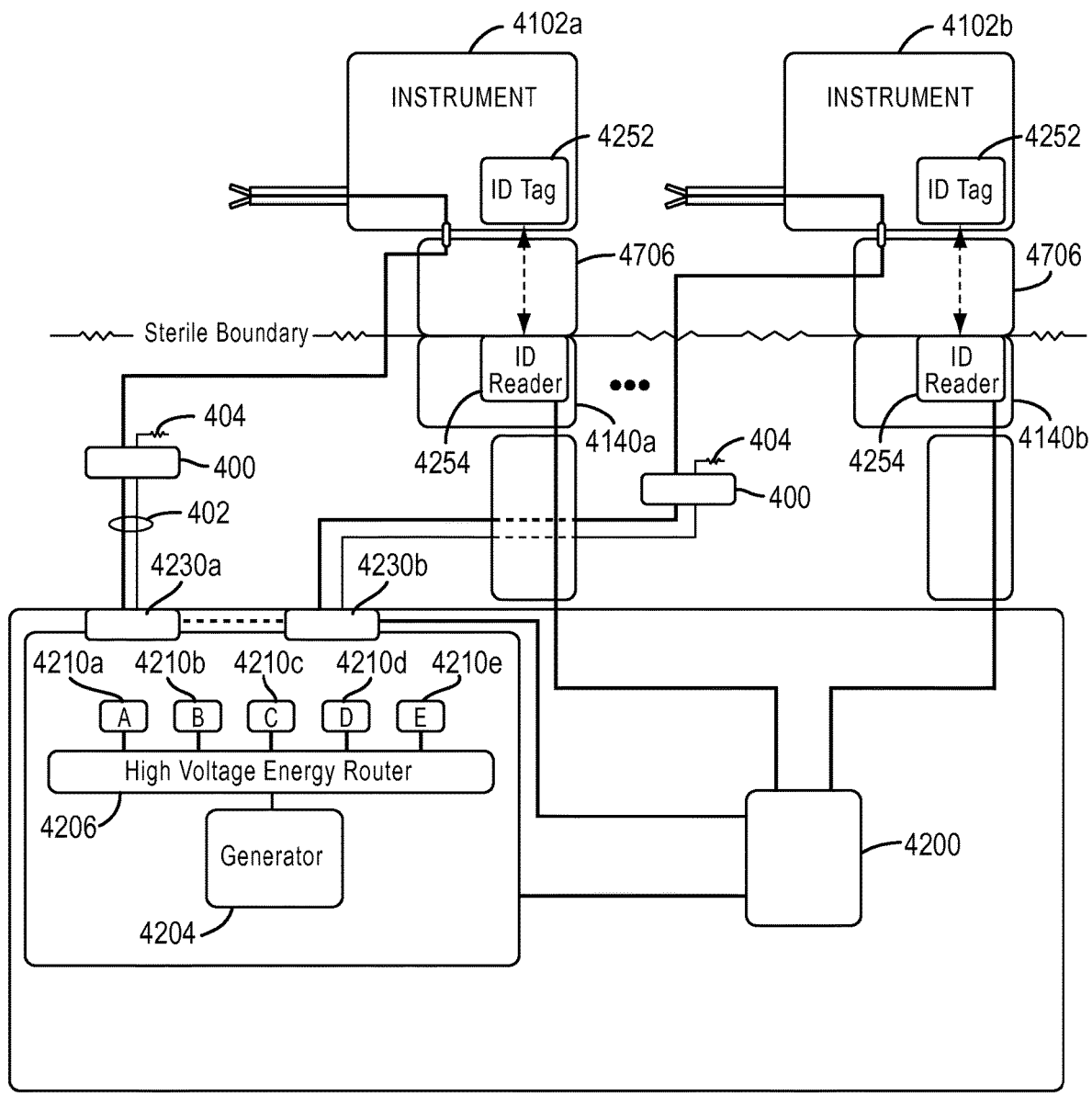
FIG. 4 is a schematic block diagram of an exemplary teleoperated surgical system in accordance with at least one exemplary embodiment.

In exemplary embodiments, the control system may have all control functions integrated in one or more processors, such as a core processor 200 at the control cart 130, or, as shown in FIGS. 2-4, additional controllers may be provided as separate units and/or supported (e.g., in shelves) on the control cart 130 for convenience. The latter may be useful, for example, when retrofitting existing control carts to control surgical instruments requiring additional functionality, for example, by providing electrical energy for use in monopolar and bipolar applications. For example, an electrosurgical unit (ESU) 202, which can provide flux sources, such as monopolar and bipolar energy sources, may be provided as separate unit(s) from the core processor 200 and supported on the control cart 130. Alternately, an ESU 202 may be incorporated with the core processor 200 at the control cart 130 into a single integrated flux source and control unit. In various exemplary embodiments, in the case of electrosurgical energy sources for example, one or more electrical energy sources can be used to provide monopolar and/or bipolar energy. Which energy is provided to an electrosurgical instrument (for example, which energy source will be commanded to supply a particular energy type) can be controlled based on mapping particular input devices (e.g., pedals) at the surgeon console to particular energy types (e.g., bipolar or monopolar).

One of ordinary skill in the art would recognize that the controllers, e.g., core processor 200, provided at control cart 130 may be implemented as part of a control system, which, as will be discussed in more detail below, controls various functions of the present disclosure. One of ordinary skill in the art would recognize that functions and features of the controllers, e.g., core processor 200, may be distributed over several devices or software components, including, but not limited to, processors at any of the surgeon console 120, patient side cart 110 and/or other devices, such as ESUs, incorporating processors therein. Functions and features of the control system, which may include core processor 200, may be distributed across several processing devices.

Flux Disambiguation System and Method

Referring now to FIG. 2, a schematic diagram is depicted which shows a block diagram of exemplary components of an exemplary teleoperated surgical system to deliver flux, e.g., electrical energy, to surgical instruments, such as electrosurgical instruments 2102, in accordance with at least one exemplary embodiment of the present teachings. The control cart 2130 may include at least one processor, e.g., core processor (or controller) 2200 that controls the operation of the electrosurgical instruments 2102 installed at a patient side cart at the patient side manipulators 2140 to which the electrosurgical instruments 2102 are coupled. In an exemplary embodiment, the core processor 2200 can control the delivery of flux (e.g., electrical energy) to the surgical instruments (two such electrosurgical instruments 2102a and 2102b being shown in FIG. 2). While only two electrosurgical instruments 2102a and 2102b are shown and described with reference to FIG. 2, one of ordinary skill in the art would recognize this number is exemplary and the flux disambiguation system would be operable with a single surgical instrument or more than two surgical instruments. Further, the principles of the present teachings would apply irrespective of the number of surgical instruments. In addition, while electrosurgical instruments are shown and described, one of ordinary skill in the art would recognize that other surgical instruments could be mounted at the patient side cart, including surgical instruments capable of supplying other types of flux, including other types of energy, fluid, vacuum pressure, imaging streams, etc. In addition, the principles of the present teachings would apply irrespective of the number of patient side manipulator arms 2140 and the present disclosure may apply to more than two patient side manipulator arms 2140 or a single patient side manipulator arm with multiple actuation interfaces.

The control cart 2130 may include a flux supply source, for example embodied as an electrosurgical unit (ESU) 2202. In various exemplary embodiments, the ESU 2202 may be disposed to transmit to and receive signals from the core processor 2200. In an alternative embodiment, the core processor 2200 and the components of the ESU 2202, which will be discussed further below, can be incorporated together at the control cart 2130 as a single integrated unit, within which at least one of the components of the ESU 2202 may be in communication to receive signals to and from the core processor 2200. As discussed above, the core processor 2200 or other controllers that are part of the control system can be provided at any device and the transmission, reception and processing of signals may be distributed across the core processor 2200 and/or any other processing devices communicating within the teleoperated surgical system, including at the surgeon console 2120, the patient side cart 2110, the control cart 2130, the ESU 2202 or a separate processing unit.

The ESU 2202 includes one or more flux (e.g., electrosurgical energy) generators 2204. For example, one or more electrical energy generators may be provided at the ESU 2202. One or more flux generators 2204 may also be provided separately from one another and/or separately from the ESU 2202. The ESU 2202 may also include, for example, a router, e.g., a high voltage energy router 2206, and a plurality of connector interfaces 2230a-2230e, corresponding to ports 2210a-2210e. A flux source pathway is defined between the one or more flux generators 2204 and the ports 2210a-2210e. The one or more flux generators 2204 are configured to provide flux, for example, electrical energy, such as high voltage cautery energy, to the electrosurgical instruments 2102 through respective ports 2210a-2210e, to which the electrosurgical instruments 2102 are respectively connected. For example, as shown in FIG. 2, electrical energy is provided from the flux generator 2204 to the electrosurgical instrument 2102a through port 2210b and to the electrosurgical instrument 2102b through port 2210c. Although a single flux generator 2204 is depicted in FIG. 2, those having ordinary skill in the art would appreciate that more than one flux source may be included in the system. For example, various flux generators can be used to supply flux, such as electrical energy, to specific types of instruments, such as a bipolar energy generator, a monopolar energy generator, and a harmonic generator. One of ordinary skill in the art would recognize that, for example, a bipolar energy generator would be used to supply energy to an electrosurgical instrument configured to receive bipolar energy, such as bipolar electrosurgical instrument 2102a, and a monopolar energy generator would be used to supply energy to an electrosurgical instrument configured to receive monopolar energy, such as monopolar electrosurgical instrument 2102b. In various exemplary embodiments, a single energy generator may be utilized but controllable, e.g., via the core processor 2200, to provide differing types of energy.

The flux generator 2204 is configured to be placed in operational flux communication with the surgical instruments 2102, which may be provided at the manipulator arms 2140. In various exemplary embodiments, the electrosurgical instrument 2102a is bipolar and configured to be placed in operational communication with the flux generator 2204 through, for example, a flux transmission conduit, such as a bipolar energy transmission cable 142. Also, in an exemplary embodiment, the electrosurgical instrument 2102b is monopolar and configured to be placed in operational communication with the flux generator 2204 through, for example, a flux transmission conduit, such as a monopolar energy transmission cable 144. The ESU 2202 may, in at least one exemplary embodiment of the present disclosure, include one or more data interface modules 208, such as, for example, an instrument identifier interface module 208 (shown in FIG. 2) and/or an actuation interface assembly identifier interface module 208*b* (shown in FIG. 3), which transmit identification data to the control system and may communicate with, for example, the core processor 2200. As will be described in more detail below, the data interface module 208 is configured to receive identification information of a device, either from a surgical instrument 2102 upon connection of the surgical instrument 2102 with the ESU 2202 or from a support structure upon connection of the ESU with an actuation interface assembly at the support structure to which the surgical instrument 2102 is installed. The data interface modules 208 may be processing devices. The one or more data interface modules 208 may alternately be provided at the control cart 2130 in communication with the core processor 2200 and in the same unit with the core processor 2200.

The flux generator 2204 may be connected to the router 2206. At least one of the surgical instruments 2102 is in communication via a flux transmission conduit, such as energy transmission cables 142, 144, with the flux generator 2204 through one of the ports 2210*a*-2210*e*. In various exemplary embodiments, as will be described in more detail below, when the surgeon (e.g., at the surgeon console 2120) provides a flux input command via input devices, a controller of the control system sends a signal to supply flux through a specific one of the ports 2210*a*-2210*e* via the flux transmission conduit 142, 144 to the surgical instrument 2102 connected to the energized port. The router 2206 may, in an exemplary embodiment, route flux, e.g., electrical energy such as high voltage cautery energy, from one or more flux generators 2204 to the respective instruments 2102*a*, 2102*b* through one of the ports 2210*a*-2210*e*.

According to at least one exemplary embodiment of the present disclosure, a plurality of connector interfaces 2230*a*-2230*e* is provided at, for example, the electrosurgical unit 2202. The connector interfaces 2230*a*-2230*e* are configured to interface with the flux transmission conduits, e.g. the bipolar energy transmission cable 142 or the monopolar energy transmission cable 144, operationally coupled to one of the surgical instruments 2102, e.g., electrosurgical instruments, at the patient side cart 2110. In an exemplary embodiment, specific ports, e.g., ports 2210*a*-2210*b*, may include a connector interface (described in more detail below) configured to connect with specific surgical instruments, such as the bipolar electrosurgical instrument 2102*a*, by the bipolar energy transmission cable 142. Electrical energy may be provided from the flux generator 2204, e.g., a bipolar energy generator, through one of the ports 2210*a*-2210*b* through the bipolar energy transmission cable 142 to the bipolar electrosurgical instrument 2102*a*. Ports 2210*c*-2210*d*, for example, may include a connector interface configured to connect with specific surgical instruments, such as the monopolar electrosurgical instrument 2102*b*, by the monopolar energy transmission cable 144. Electrical energy may be provided from the flux generator 2204, e.g., a monopolar energy generator, through one of the ports 2210*c*-2210*d* through the monopolar energy transmission cable 144 to the monopolar electrosurgical instrument 2102*b*. Those having ordinary skill in the art will appreciate that the ports could have numerous configurations and be arranged and/or distributed among one or more flux supply sources.

In accordance with at least one exemplary embodiment of the present disclosure, each of the specific surgical instruments 2102, e.g., electrosurgical instruments 2102*a*, 2102*b*, includes a unique identifier identifying the specific electrosurgical instrument 2102*a*, 2102*b*. The unique identifier may be, for example, a unique serial number for the specific electrosurgical instrument 2102*a*, 2102*b*. The unique identifier may be encoded at the electrosurgical instrument 2102 at a readable or readable and writable memory structure. According to one exemplary embodiment of the present disclosure, a unique identifier is encoded at an electronic circuit, such as an EPROM or EEPROM electronic chip 280, disposed at the surgical instrument 2102. In addition, according to at least one exemplary embodiment of the present disclosure, the surgical instrument 2102 includes a transmitter, e.g., a radio frequency identification (RFID) tag 2252, at which is also encoded the unique identifier. According to exemplary embodiments of the present disclosure, each of the manipulator arms 2140*a*-2140*d* includes a receiver, such as an RFID reader 2254, configured to sense the information transmitted from the RFID tag 2252 corresponding to an electrosurgical instrument 2102. The transmitter and the receiver may both support various wireless communication protocols, with which those of ordinary skill in the art would be familiar.

One of ordinary skill in the art would recognize that the receiver, such as the RFID reader 2254, may be provided at any structure to which the actuation interface assembly is attached. For example, the actuation interface assembly 706 of FIG. 8 may be connected to a manipulator arm through a support structure 702 (also shown in FIG. 8) at the arm, or may be provided at a drape 704 (shown in FIG. 8) attached to one of the manipulator arms or at an adapter 700 at one of the manipulator arms.

The surgical instrument 2102 is installed at an actuation interface assembly 2700, which may be attached to one of the manipulator arms 2140. One of the flux transmission conduits, e.g., energy transmission cables 142, 144, can connect the surgical instrument 2102 that is installed at the actuation interface assembly 2706 (or at a sterile adapter (e.g., sterile adapter 706) associated with an actuation interface assembly) to a flux supply pathway, e.g., through ports 2210*a*-2210*e* connected with the one or more flux generators 2204 at the electrosurgical unit 2202 or at ports at the control cart 2130 individually connected to separate flux generators, through a sterile boundary.

When the energy transmission cables 142, 144 connect the surgical instruments 2102 through the flux supply pathway at the electrosurgical unit 2202 or the control cart 2130, an instrument identification signal indicative of the unique identifier that is encoded at, for example, an electronic chip 280 of the instrument, is output to one of the flux source connector interfaces 2230*a*-2230*e* corresponding to the ports 2210*a*-2210*e*. The first instrument identification signal may be transmitted through a data transmission line of the various energy transmission cables 142, 144 in accordance with the present disclosure and described in more detail below. For example, as set forth further below, a data transmission terminal 221 or 225 (see FIGS. 9A and 11A) of the energy transmission cables 142, 144 may output the first instrument identification signal. The first instrument identification signal may be read by the instrument identifier interface module 208, which determines the unique identifier of the specific electrosurgical instrument 2102*a* from the first instrument identification signal. In an alternative embodiment, the first instrument identification signal may be provided directly to the core processor 2200 along with, for example, information regarding the flux supply pathway, e.g., through ports 2210a-2210e, to which the surgical instrument 2102 is operationally-coupled. The first instrument identification signal may also include other information, such as a flux delivery type of the surgical instrument 2102. The flux delivery type may indicate, for example, the type of flux the surgical instrument 2102 transmits, e.g., electrical energy, fluid, vacuum pressure, etc. and may also identify, for example, whether the instrument 2102 requires bipolar or monopolar energy.

Upon receiving and reading the first instrument identification signal through a specific connector interface 2230a-2230e corresponding to a specific port 2210a-2210e, the instrument identifier interface module 208 may identify which one of the flux supply pathways, e.g., through ports 2210a-2210e, is operationally-coupled with the specific instrument 2102 that transmitted the first instrument identification signal. For example, as shown in FIG. 2, the instrument identifier interface module 208 may identify that port 2210b is operationally-coupled to the bipolar electrosurgical instrument 2102a. One of ordinary skill in the art would recognize that the instrument identifier interface module 208 need not be disposed within ESU 2202 and may be provided separately from ESU 2202, for example, incorporated into another processing unit, such as core processor 2200, etc. The instrument identifier interface module 208 may provide the associated data, which identifies the operationally-coupled pair of the surgical instrument and the port 2210a-2210e, to the core processor 2200.

When the electrosurgical instrument 2102a is installed at an actuation interface assembly 2706 at a specific manipulator arm 2140, a second instrument identification signal is output from, for example, the RFID tag 2252 associated with the electrosurgical instrument 2102a and is read by the RFID reader 2254. The RFID reader 2254 provides instrument identification information to, for example, the core processor 2200 identifying a specific surgical instrument 2102. When the RFID reader 2254 provides the instrument identification information to the core processor 2200, the core processor 2200 recognizes that the instrument identification information is associated with a specific actuation interface assembly 2706. Any structure to which the actuation interface assembly 2706 is coupled, e.g., other kinematic support structures, such as, for example, the manipulator arm 2140 or alternatively the drape 704 or the adapter 700 in the embodiment of FIG. 8, etc., may be provided with the reader 2254 that reads the instrument identification signal. The control system is therefore able to determine that the instrument identification signal is associated with a specific actuation assembly that is coupled to the structure that read the instrument identification signal. For example, as shown in FIG. 2, when the electrosurgical instrument 2102a is installed at the manipulator arm 2140a, the RFID reader 2254 at the manipulator arm 2140a reads the output instrument identification signal from the electrosurgical instrument 2102a and notifies the core processor 2200 that the electrosurgical instrument 2102a is installed at an actuation interface assembly 2706 at the manipulator arm 2140a.

The control system therefore receives information that identifies that a specific surgical instrument 2102 is operationally-coupled to a specific flux supply pathway, e.g., from one of the flux generators 2204 through one of ports 2210a-2210e. The control system also receives information that the specific surgical instrument 2102 is associated with a specific actuation interface assembly. Thus, the control system is able to identify that a remotely-controllable kinematic flux delivery structure, which includes the identified surgical instrument 2102 coupled to a specific actuation interface assembly at, for example, manipulator arm 2140, is operationally-coupled to a particular flux supply pathway, e.g., through one of the ports 2210a-2210e.

In addition, the control system recognizes which of the input devices at the surgeon console is operationally coupled to a specific kinematic structure. For example, the control system maps one of the input devices to a structure to which the actuation interface assembly is coupled. Therefore, because the specific surgical instrument 2102 has been identified as being coupled to the actuation interface assembly 2706 coupled with a specific structure, e.g., manipulator arm 2140, the control system is able to determine that a particular remotely-controllable kinematic flux delivery structure is operationally coupled to the input device that has been mapped to the specific structure to which the actuation interface assembly 2706 is coupled. Thus, when flux is selected to be supplied to the identified surgical instrument 2102 of a specific remotely-controllable kinematic flux delivery structure, then the control system sends a signal to cause flux to be supplied through a particular port, e.g., ports 2210a-2210e, that is recognized as being operationally-coupled to the specific remotely-controllable kinematic flux delivery structure.

The core processor 2200 may provide a routing signal to the router, e.g., energy router 2206, to direct the energy router 2206 to route energy through the respective port (e.g., port 2210b, 2210c) determined to be operationally-coupled with the respective instruments 2102a, 2102b installed at the actuation interface assemblies 2706 of the respective arms 2140a-2140d. Thus, as the control system is able to indicate which port 2210a-2210e should be provided with energy based on which actuation interface assemblies 2706 at one of arms 2140a-2140d a specific electrosurgical instrument 2102 is installed, then the input devices 124a-124d can be mapped to a specific electrosurgical instrument 2102 installed at an actuation interface assembly 706 at a particular manipulator arm 2140a-2140d.

In various exemplary embodiments, some of the input devices 124 can be assigned by the core processor 2200 to operate functions (e.g., monopolar, bipolar) of the instruments, e.g, electrosurgical instrument 2102a, 2102b that are currently installed and being controlled by a user at the surgeon console 120. Such mapping of the input device at the surgeon console 120 to perform functions of instruments at the patient side car can be either functional or positional. In the former, for example, a particular foot pedal 124a-124d is assigned to cause bipolar energy to be supplied from the electrical flux supply source (e.g., ESU). In the latter, for example, a left bank of foot pedals 124a, 124b is assigned to cause energy delivery to an instrument controlled by the left gripping input device 122 of the surgeon side console and the right bank of pedals 124c, 124d to operate the energy function of an instrument controlled by the right gripping input device 122. For this and other positional mapping that can be utilized for mapping of input devices at the surgeon side console to instruments at the patient side console, reference is made to U.S. patent application Ser. No. 14/028,006, filed Sep. 16, 2013 (for "METHODS AND SYSTEMS FOR ASSIGNING INPUT DEVICES TO TELEOPERATED SURGICAL INSTRUMENT FUNCTIONS"), and to U.S. Provisional Application No. 61/702,166, filed Sep. 17, 2012 and to which U.S. patent application Ser. No. 14/028,006 claims priority, both of which are incorporated by reference herein. Thus, for example, because the system recognizes that the electrosurgical instrument 2102a is installed at the actuation interface assembly 2706 coupled to a particular manipulator arm 2140a and recognizes the instrument type, then based on the mapping, the system is able to provide the correct type of energy to the instrument 2102a upon receiving a command from whichever pedal 124a-124d is determined to be mapped to the instrument 2102a.

When the core processor 2200 associates one of the ports 2210a-2210e with an actuation interface assembly to which a specific electrosurgical instrument 2102 is coupled, the control system can provide feedback to a user indicating the operationally coupled pair of the remotely-controllable kinematic flux delivery structure and the specific port 2210a-2210e, causing the feedback to be output, for example, at the display 126 and/or display 132. The output can include, for example, the location where the instrument is installed and the type of the instrument (e.g., bipolar or monopolar).

Turning now to FIG. 3, in accordance with at least one exemplary embodiment of the present disclosure, instead of energy transmission cables 142, 144 directly connecting the electrosurgical unit 2202 to the surgical instrument 2102, as in the exemplary embodiment of FIG. 2, an energy transmission cable 302 may extend from the electrosurgical unit 3202 through the manipulator arms 3140a to instrument 3102a. Similar to the energy transmission cables 142, 144, the energy transmission cable 302 includes an electrical energy transmission line to provide energy between a flux generator 3204 and the surgical instrument 3102. The energy transmission cable 302 also includes a data signal transmission line to provide data identifying, for example, the manipulator arm 3140 to which an identified surgical instrument 3102 is operationally coupled by an actuation interface assembly 3706. The identification data is provided to a data interface module 3209, which may be provided at the electrosurgical unit 3202 or at the control cart 3130, and which may communicate with a processing device of the control system, such as core processor 3200. One or more auxiliary cables 304 may be disposed in each of the manipulator arms 3140 through to the actuation interface adapter 3700 or, in an alternative embodiment, may be disposed through a sterile drape to the actuation interface adapter 3700. The auxiliary cables 304 are configured to be placed in flux communication with the energy transmission cable 302.

Similarly to the embodiment disclosed in FIG. 2, a unique identifier is encoded at each of the instruments 3102 and a transmitter 3252 transmits an instrument identification signal which is read by the receiver 3254. The receiver 3254 in an exemplary embodiment may be disposed at the manipulator arm 3140a, 3140b or at actuation interface assemblies 3700. The receiver 3254 may output an instrument identification signal, which can be received by the core processor 3200. In an installed position at an actuation interface assembly 3700, an electrosurgical instrument 3102 is thus operationally coupled to a flux supply source, for example, the electrosurgical unit 3202, through the cables 302 and 304. In accordance with exemplary embodiments of the present disclosure, the energy transmission cable 302 is connected to the flux generator 3204, for example, of the electrosurgical unit 3202 via one of the ports 3210a-3210e. The cable 302 also is connected to a manipulator arm 3140, and ultimately at the actuation interface assembly 3700, to which the surgical instrument 3102 is operationally coupled. A data interface 3300 at the manipulator arm 3140 identifies the manipulator arm 3140 to which the flux transmission conduit, e.g., energy transmission cable 302, is connected and provides manipulator arm identification information to a data interface module, such as manipulator arm interface module 3209, at the electrosurgical unit 3202 or at the control cart 130 and in communication with, for example, the core processor 3200. The data interface module 3209 provides information to the core processor 3200 identifying the respective manipulator arm 3140a and the port 3210b, to which the manipulator arm 3140a is connected by the energy transmission cable 302. The core processor 3200 then is able to associate the identified instrument 3102, e.g., instrument 3102a installed at an actuation interface assembly 3700 at, for example, the identified manipulator arm 3140a, with the port 3210b operationally coupled to the identified manipulator arm 3140a. Thus, the processor 3200 can determine the port 3210b through which flux should be supplied upon receipt of an input command to energize the instrument 3102a. Thereafter, in response to an input command signal at one of the input devices of a surgeon console (e.g., input device 124) intended for a specific kinematic flux delivery structure, including a specific surgical instrument 3102a operationally coupled with an actuation interface assembly coupled to an identified manipulator arm 3140a, the control system can send a signal to supply flux from the port 3210b that is operationally coupled to the specific kinematic structure.

In accordance with another exemplary embodiment of the present disclosure, instead of providing the identification of the manipulator arm 3140 to the data interface module 3209 at, for example, the electrosurgical unit 3202, one of ports 3210a-3210e, could be identified to the data interface 3300 at the manipulator arm 3140. For example, port 3210b could provide a port identification through the data signal transmission line of the energy transmission cable 302 to the manipulator arm 3140a or any other structure to which the actuation interface assembly is coupled, and the manipulator arm 3140a could provide data to, for example, the core processor 3200 indicating the instrument identification of, e.g., electrosurgical instrument 3102a and the port identification of, e.g., port 3210b. In accordance with an exemplary embodiment, the core processor 3200 then can associate the identified instrument 3102a installed at the actuation interface assembly at the specific manipulator arm 3140a (i.e., the remotely-controllable kinematic flux delivery structure) that provided the instrument identification with the port 3210b in communication with the manipulator arm 3140a including the actuation interface assembly to determine the port 3210a-3210e, e.g., port 3210b, to which the instrument 3102, e.g., instrument 3102a, is electrically connected. Thereafter, in response to an input at one of the input devices 124, the core processor 3200 can output a signal to supply flux from the port 3210a-3210e, e.g., port 3210b, that is operationally coupled to a selected kinematic structure (including the surgical instrument 3102 operationally coupled to the actuation interface assembly). The signal may cause flux to be supplied by routing the flux from a flux generator 3204 through one of the ports 3210a-3210e.

Figure 8:
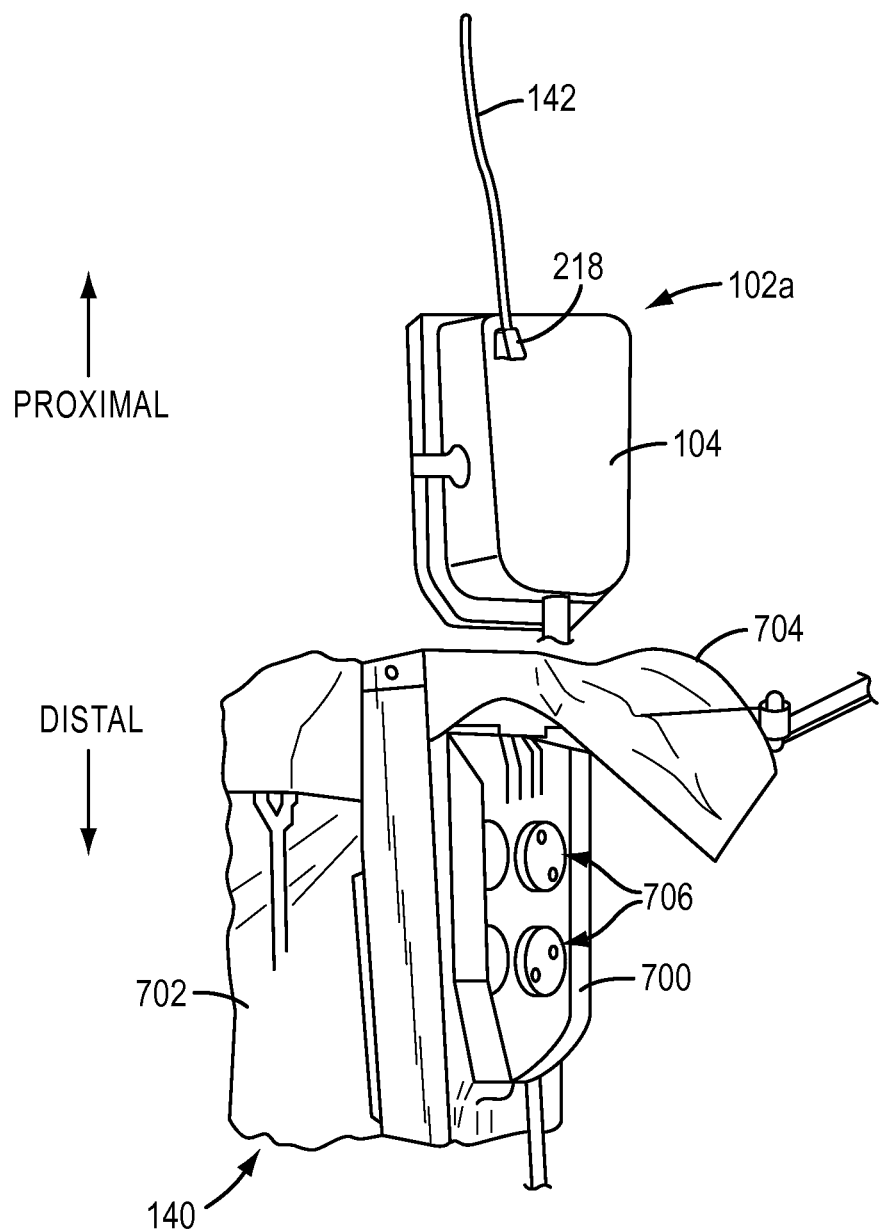
FIG. 8 is a perspective view of an actuation interface assembly at a patient side cart of a teleoperated surgical system in accordance with at least one exemplary embodiment.

Referring now to FIG. 4, according to another exemplary embodiment, an alternative connection scheme between a flux transmission conduit and a surgical instrument. FIG. 4 illustrates a flux transmission conduit, such as energy transmission cable 402, for example, that is disposed through a sterile drape (such as drape 704 in FIG. 8) and is connected at a drape connection point 400 to a connector, e.g., a socket (not shown). An energy transmission cable 402 also extends to the actuation interface assembly 4706 to which the surgical instrument 4102 is attached. With reference to FIG. 8, the drape connection points 400 can include a socket disposed on a support structure 702 to which the actuation interface assemblies 700 are mounted. Each socket at the respective support structures can have a different value resistor that can be detected. For example, with reference again to FIG. 4, a presence detection resistor 404 at the drape connection point 400 can detect the resistance value and provide an identification through the data signal transmission line of the energy transmission cable 402 of the support structure (e.g., support structure 702) provided at manipulator arm, e.g., arm 4140a, to which the drape (e.g., drape 704 in FIG. 8) is connected at the drape connection point 400. The identification information of the support structure 702 may be provided directly to the core processor 4200 with information as to the port 4210a to which the drape 704 housing the energy transmission cable 402, which is connected with the manipulator arm 4140, is connected. Alternately, the identification information may be provided to a data interface module (not shown in FIG. 4; see FIGS. 2 and 3), which may be provided at, for example, the electrosurgical unit 4202. In addition, similarly to the embodiments disclosed in FIGS. 2 and 3, a unique identifier is encoded at each of the instruments 4102a, 4102b and a transmitter 4252 transmits an instrument identification signal which is read by a receiver 4254, for example, coupled to an arm 4104 or support structure on an arm 4140a, 4140b. An instrument identification signal is output from the receiver 4254 to the control system, including, e.g., the core processor 4200. The control system then associates the identified instrument, e.g., instrument 4102a, with the identified arm, e.g., arm 4140a, and the port, e.g., port 4210b, connected to the arm 4140a by the energy transmission cable 402 within the drape. Thereafter, in response to an input at one of the input devices, such as input devices 124, the control system can output a signal to cause flux to be supplied through a particular port, e.g., port 4210b, and one of a corresponding interface, e.g., one of interface 4230a . . . 4230b, to a selected kinematic flux delivery structure (which includes the identified instrument coupled to an actuation interface assembly coupled to, for example, the identified arm 4140a).

One of ordinary skill in the art would recognize that the information indicative of the association between the above-described elements (e.g., the electrosurgical instrument, the flux supply pathway (including the ports), the arm or other support structure to which the actuation interface assembly is coupled, etc.) may be transmitted to the core processor 200, 2200, 3200, and 4200 at control cart 130, 2130, 3130, and 4130 or may be distributed across multiple control devices, including, but not limited to, processors at the surgeon console 120, processors at the patient side cart 110, processors provided at or in communication with control cart 130, 2130, 3130, and 4130 or core processor 200, 2200, 3200, and 4200 at control cart 130, 2130, 3130, and 4130, etc. One of ordinary skill in the art would recognize that the information indicative of the association between the above-described elements may occur at any of the described processing or control elements, collectively referred to as a control system.

Figure 5:
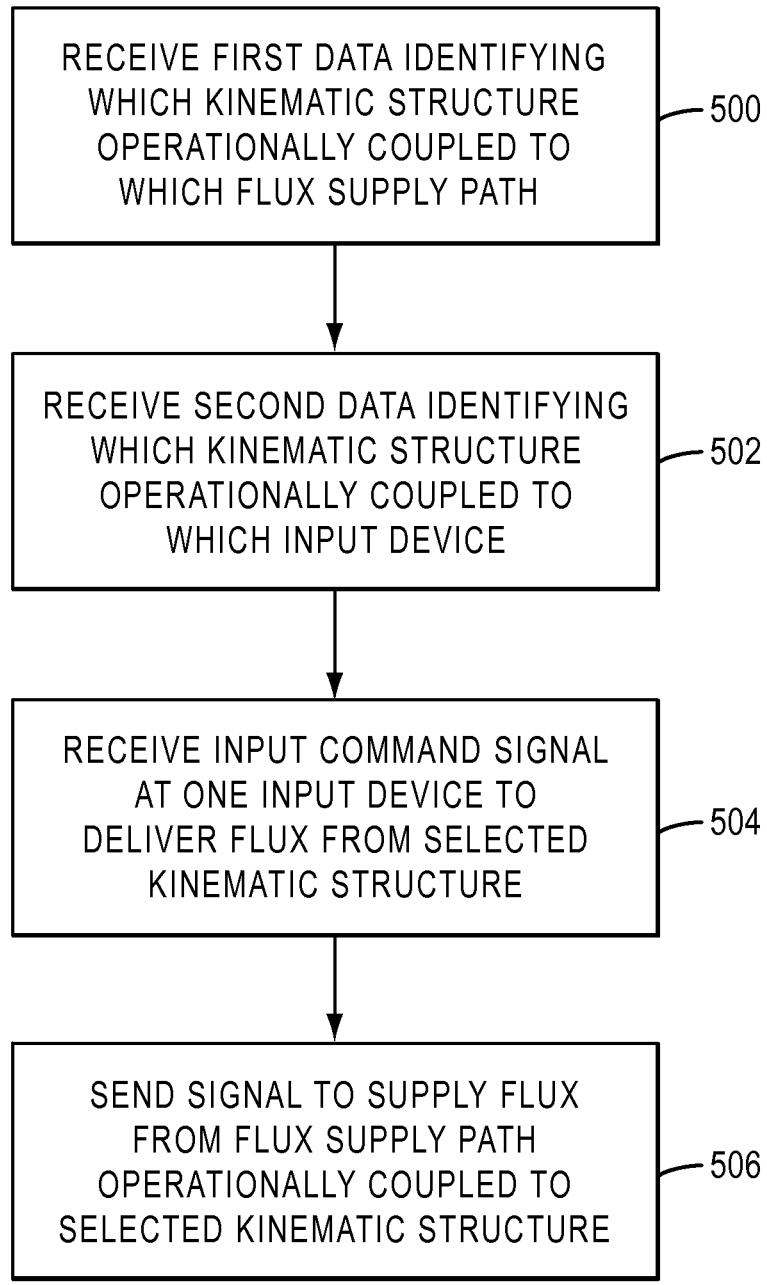
FIG. 5 is a flow diagram illustrating an exemplary workflow for controlling flux delivery to a surgical instrument of a teleoperated surgical system in accordance with at least one exemplary embodiment.

Turning now to FIG. 5, the teleoperated surgical system 100 as shown and described in FIG. 1 and in the exemplary embodiment of FIG. 2 is used to illustrate an the implementation of the present disclosure, which contemplates providing a method and system for delivering flux, e.g., electrical energy, fluid, etc. to a surgical instrument 102, e.g., an electrosurgical instrument. FIG. 5 is an exemplary embodiment of a workflow for determining which of a plurality of flux supply pathways is to be supplied with flux, which is dependent on a selected kinematic structure to which the flux supply pathway is operationally coupled. In various exemplary embodiments in accordance with the present disclosure, in the exemplary workflow of FIG. 5, at operation 500 first data is received by, for example, the control system, that identifies which of a plurality of remotely-controllable kinematic flux delivery structures, which includes the surgical instrument 102 operationally coupled to an actuation interface assembly at a manipulator arm 140 of a patient side cart 110, is operationally coupled to which of a plurality of flux supply pathways, e.g., through ports 2210a-2210e. At operation 502, second data may be received at the control system that identifies which of the remotely-controllable kinematic flux delivery structures is operationally coupled to which of the plurality of input devices at the surgeon console. The input devices may be mapped in advance to operate functions that are available from the instrument(s) 102 being controlled (such mapping can include, for example, functional or positional mapping), and the control system is able to identify which remotely-controllable kinematic flux delivery structure is operationally coupled to which of the input devices. For exemplary positional mapping techniques that can be utilized, reference is made to U.S. patent application Ser. No. 14/028,006, filed Sep. 16, 2013 (for "METHODS AND SYSTEMS FOR ASSIGNING INPUT DEVICES TO TELEOPERATED SURGICAL INSTRUMENT FUNCTIONS"), and to U.S. Provisional Application No. 61/702,166, filed Sep. 17, 2012, both incorporated by reference herein.

At operation 504, an input command signal is received at one input device to deliver flux from a selected remotely-controllable kinematic flux delivery structure. Then, at operation 506, a signal is transmitted to supply flux from the respective flux supply pathway, e.g., through one of the ports 2210a-2210e, that is operationally coupled to the selected remotely-controllable kinematic flux delivery structure. The control system transmits the signal to supply flux after determining which of the flux source pathways, e.g., one of the flux generators 2204 in communication with one of the ports 2210a-2210e, is operationally coupled to which of the kinematic flux delivery structures in order to cause flux to be supplied from a flux generator through the appropriate port 2210a-2210e to a selected remotely-controllable kinematic flux delivery structure that is operationally coupled to one of the plurality of input devices that generate input command signals to control the remotely-controllable kinematic flux delivery structures.

One of ordinary skill in the art would recognize that when data is received by a control system, the data may be received at one or more of the controllers or processors described above as part of the control system. Further, the receipt of and/or processing of the data may be distributed across one or more of the controllers or processors of the control system.

Flux Transmission Conduits and ESU Interface

In accordance with various exemplary embodiments, flux transmission conduits are provided that connect a flux delivery device, e.g., electrosurgical instrument 102, and a flux supply source. The flux transmission conduits are provided with a flux delivery transmission line, which provides for the transmission of flux from the flux supply source to the flux delivery device. In addition, the flux transmission conduits are also provided with a data signal transmission line that provides for the transmission of data, such as flux delivery device identification data, from the flux delivery device through a flux supply pathway connector interface to a data signal processor, e.g., data interface module 208. Thus, in providing the identification data, the flux transmission conduit facilitates the ability of the control system to determine, through the reception of the identification data, an association between the kinematic flux delivery structure (including the flux delivery device) and a flux supply pathway (e.g., from the flux supply source through a port). The association between the kinematic flux delivery structure and the flux supply pathway enables the system to determine from which of the flux supply pathways that flux is to be supplied when flux is intended for a specific kinematic flux delivery structure.

Figure 9A:
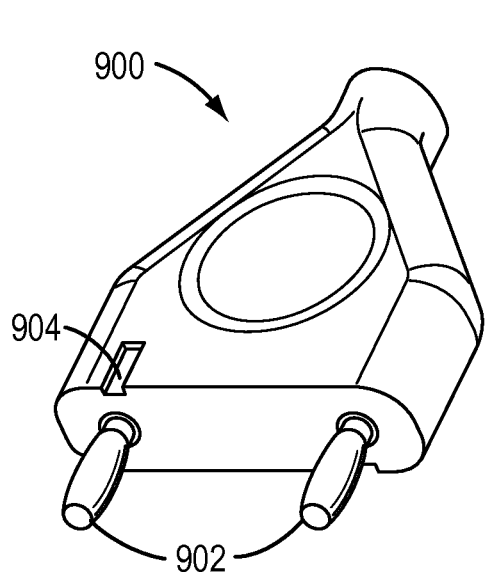
FIG. 9A is a perspective view of a connector interface of an energy transmission cable in accordance with one exemplary embodiment.
Figure 9B:
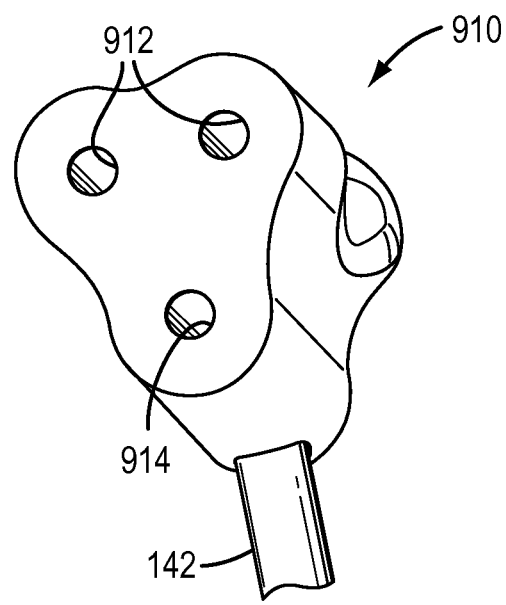
FIG. 9B is a perspective view of a connector interface of an energy transmission cable in accordance with one exemplary embodiment.
Figure 9C:
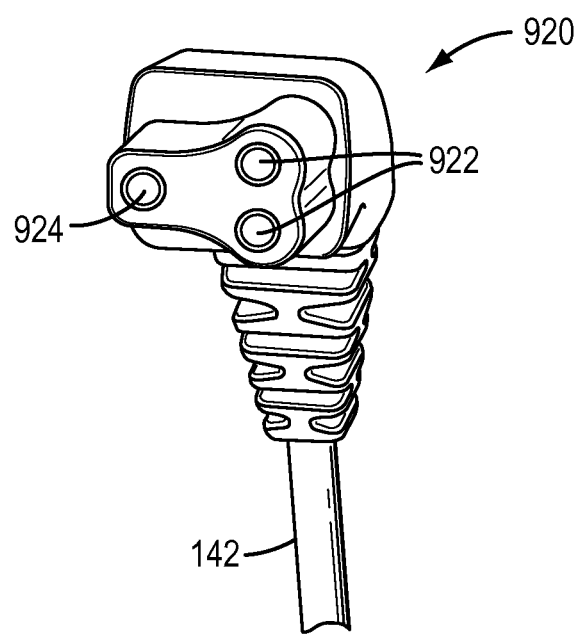
FIG. 9C is a perspective view of another exemplary embodiment of a connector interface of an energy transmission cable.
Figure 10A:
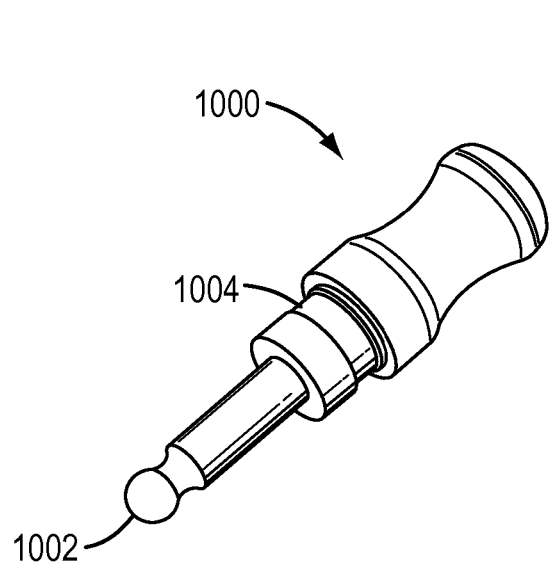
FIG. 10A is a perspective view of a connector interface of an energy transmission cable in accordance with yet another exemplary embodiment.
Figure 10B:
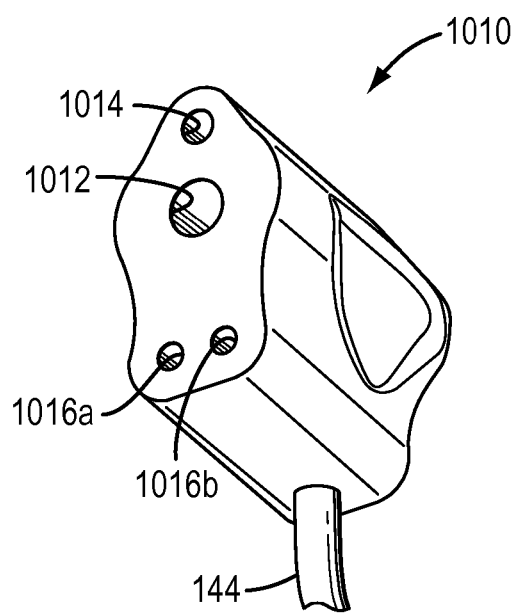
FIG. 10B is a perspective view of a connector interface of an energy transmission cable in accordance with another exemplary embodiment.
Figure 10C:
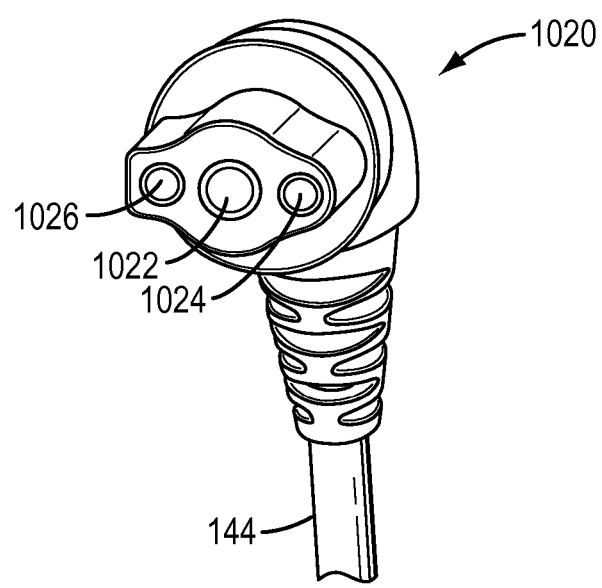
FIG. 10C is a perspective view of yet another exemplary embodiment of a connector interface of an energy transmission cable.
Figure 11:
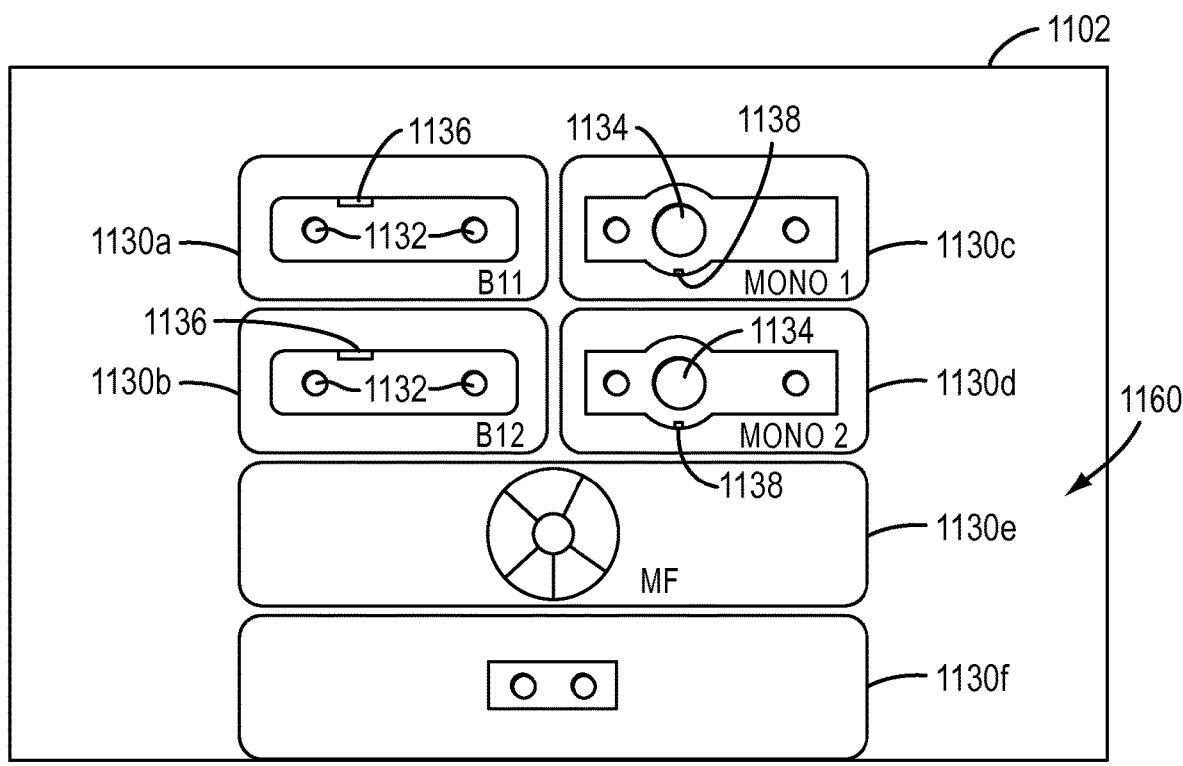
FIG. 11 is a front view of a front panel of an electrosurgical generator unit in accordance with at least one exemplary embodiment.

FIGS. 9A-9C show exemplary embodiments of flux supply source connector interfaces of a flux transmission conduit (conduits 142 partially shown in FIGS. 9B and 9C) in accordance with exemplary embodiments, and FIGS. 10A-C show exemplary embodiments of surgical connector interfaces of a flux transmission conduit (conduits partially shown in FIGS. 10B and 10C) in accordance with other exemplary embodiments. FIG. 11 shows an exemplary embodiment of a front panel of flux supply source connector interfaces. FIGS. 12A and 12B show exemplary embodiments of flux delivery instrument connector interfaces. While various exemplary embodiments herein describe flux transmission conduits that transmit electrosurgical energy, e.g., cautery energy, one of ordinary skill in the art would recognize that flux transmission conduits in accordance with the present disclosure can transmit any of a variety of fluxes, including, but not limited to laser energy, ultrasound energy, fluids, gases, radio frequency energy, nerve stimulation energy (e.g., for nerve identification and/or causing associated muscle contraction) image and/or audio streams, vacuum pressure, etc., with modifications made to the conduit structure and/or connectors as those having ordinary skill in the art would appreciate.

According to an exemplary embodiment, flux transmission conduits can include both a flux transmission line and a data signal transmission line, with the latter being configured to transmit data, for example from a memory chip. Also, in various exemplary embodiments, as discussed above with reference to FIGS. 2-5, the flux transmission line may be an electrical energy transmission cable configured to delivery bipolar or monopolar electrical energy, for example.

In an exemplary embodiment, the flux transmission conduit may be a bipolar energy transmission cable, such as bipolar energy transmission cable 142. FIG. 9A shows a first connector interface 900 configured to connect with flux supply source connector interfaces 1130a, 1130b (shown in FIG. 11), which in an exemplary embodiment may be provided at an electrosurgical unit (ESU) 1102. FIGS. 9B and 9C show different configurations of another connector interface 910, 920 of the bipolar energy transmission cable 142 configured to connect with a bipolar electrosurgical instrument 1202 at an instrument connector interface 1200 (shown in FIG. 12).

As shown in FIG. 9A, the connector interface 900 includes two male flux transmission terminals 902, configured to be placed in electrical energy contact with female terminals of a connector interface of a flux supply source, such as flux supply source 1102 of FIG. 11. The connector interface 900 is configured to engage with a corresponding flux source connector interface to transmit flux from the flux supply source through the cable 142. In addition to the terminals 902, the connector interface 900 includes a data signal transmission terminal 904, which may be, for example, an electrical pad, such as a copper pad. While a single data signal transmission terminal 904 is shown in FIG. 9A, two data signal transmission terminals, for example, two copper pads, may be provided on the top and the bottom of the connector interface 900 to allow for connection to a corresponding connector interface at, for example, an electrosurgical unit in either orientation in which the connector interface 900 would be in a connected state. The data signal transmission terminal 904 transmits identification data from, e.g., from a bipolar electrosurgical instrument 1202 (shown in FIG. 12) to a data signal processor, e.g., such as data interface module 208 or 309. Specifically, the data signal transmission terminal 904 is an interface of a data signal transmission line extending through the bipolar energy transmission cable 142. When the bipolar energy transmission cable 142 interfaces with, for example, an electrosurgical instrument that is provided with identification data, the identification data is provided from the electrosurgical instrument through the data signal transmission line to the data signal transmission terminal 904.

Referring to FIG. 11, in an exemplary embodiment, a front panel 1160 of a flux supply source 1102, e.g., ESU, is provided with a plurality of flux supply source connector interfaces 1130a-1130e configured to interface with a connector interface of an energy transmission cable. Each of the flux source connector interfaces 1130a-1130e corresponds with a specific port, e.g., one of ports 2210a-2210e, 3210a-3210e, or 4210a-4210e. Connector interfaces 1130e and 1130f may be, for example, a standard electrical connection interface 1130e or a patient return connection interface 1130f to connect with a patient return electrode (not shown).

According to an exemplary embodiment of the present disclosure, connector interfaces, such as bipolar connector interfaces 1130a, 1130b, are configured to receive the connector interface 900 of the bipolar energy transmission cable 142. The bipolar connector interfaces 1130a, 1130b each include a pair of female flux transmission terminals 1132 spaced laterally apart from one another and configured to facilitate the transmission of electrical energy from the flux generator 204. The bipolar connector interfaces 1130a, 1130b also include a data signal transmission terminal 1136 spaced vertically from the female flux transmission terminals 1132. In the exemplary embodiment of FIG. 11, the data signal transmission terminal 1136 is an electrical finger or recess configured to make contact with the terminal 904 of FIG. 9A. In an exemplary embodiment, the terminal 1136 may be a copper terminal. The data signal transmission terminal 1136 can receive identification data from, e.g., the bipolar electrosurgical instrument 1202 (shown in FIG. 12) to provide it to a data signal processor, e.g., data interface module 208. Specifically, the data signal transmission terminal 1136 is in data signal communication with the data signal processor.

The connector interface 900 of the bipolar energy transmission cable 142 is configured to mate with the bipolar flux source connector interfaces 1130a, 1130b. The male flux transmission terminals 902 are configured to be received in the female flux transmission terminals 1132. When electrical energy is supplied through one of the bipolar connector interfaces 1130a, 1130b, the energy is transmitted from a flux generator via the female flux transmission terminals 1132 to the energy transmission line of the bipolar energy transmission cable 142. The data signal transmission terminal 904 of the bipolar energy transmission cable 142 is configured to interface with the corresponding data signal transmission terminal 1136 at one of the bipolar flux source connector interfaces 1130a, 1130b. Identification data of the electrosurgical instrument 1202 is provided through the data signal transmission terminal 904 and data transmission line of the cable 142 to the corresponding data signal transmission terminal 1136, which provides the identification data to a data signal processor, e.g., data interface module 208. The data signal processor may be provided at the ESU 1102.

In addition to being configured to be received at a flux supply source connector interface 1130a, 1130b of the present disclosure, the connector interface 900 of the bipolar energy transmission cable 142 is configured to mate with a standard flux supply source connector interface of, for example, a conventional electrosurgical unit (not shown). In particular, the flux transmission terminals 902 are also configured to mate with, and supply flux from, corresponding flux transmission terminals of a conventional flux supply source. Thus, users of the bipolar transmission cable 142 of FIGS. 9A-9C are not required to use an extra cable when converting between the ESU 1102 (including the flux source connector interface 1130, 1130b) of the present disclosure and a conventional flux supply source connector interface that does not include, for example, a bipolar connector interface with a data terminal.

Figure 12:
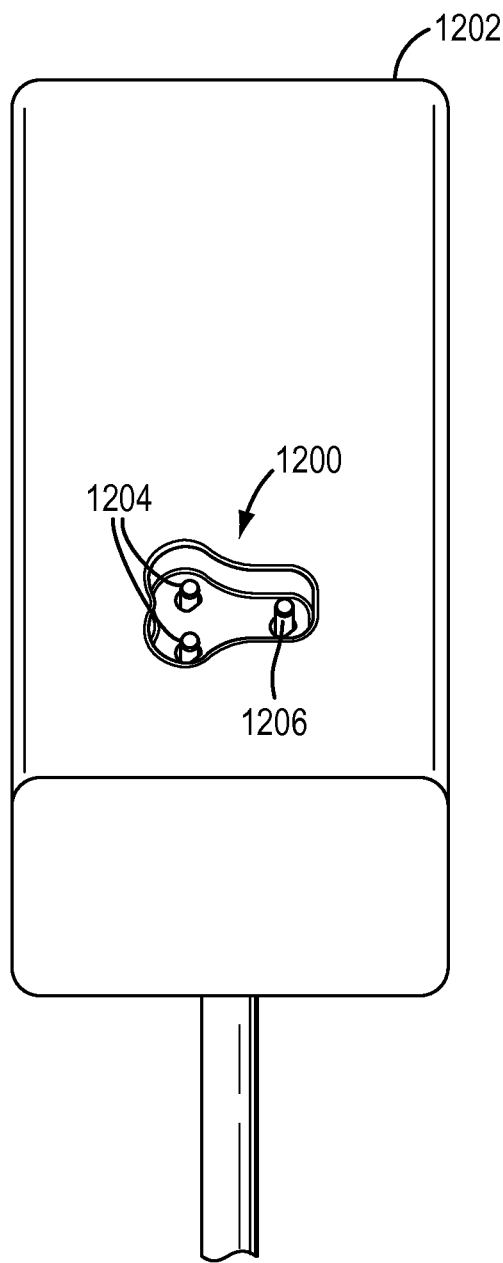
FIG. 12 is a top view of a connector interface of an electrosurgical instrument in accordance with one exemplary embodiment.

Turning now to FIGS. 9B and 9C, connector interfaces 910, 920 at the opposite end of connector interface 900 and for connection with a bipolar surgical instrument 1202 (the housing portion of the instrument that interfaces with an actuation interface assembly at the patient side cart being shown in FIG. 12) are shown. The connector interfaces 910, 920 include a pair of flux transmission terminals 912, 922, which are female connectors in the exemplary embodiment of FIGS. 9B and 9C, spaced apart from one another. The connector interfaces 910, 920 are configured to engage with a corresponding instrument connector interface, such as a conventional connector interface 1400 shown in FIG. 14, and also are configured to engage with the instrument connector interface 1200 of the bipolar electrosurgical instrument 1202 according to an exemplary embodiment, shown in FIG. 12. The connector interfaces 910, 920 are configured to transmit flux to the instrument, e.g., electrosurgical instrument 1202, through the bipolar energy transmission cable 142. Each pair of the flux transmission terminals 912, 922 is configured to engage with a corresponding pair of male flux transmission terminals 1404, shown in FIG. 14, at a connector interface 1400 of a conventional bipolar electrosurgical instrument 1402 and provide electrical energy thereto. As will be discussed in more detail below, each set of the flux transmission terminals 912, 922 is also configured to engage with a corresponding set of male flux transmission terminals 1204, shown in FIG. 12, at an instrument connector interface 1200 on a bipolar electrosurgical instrument 1202 in accordance with an exemplary embodiment of the present disclosure.

Figure 14:
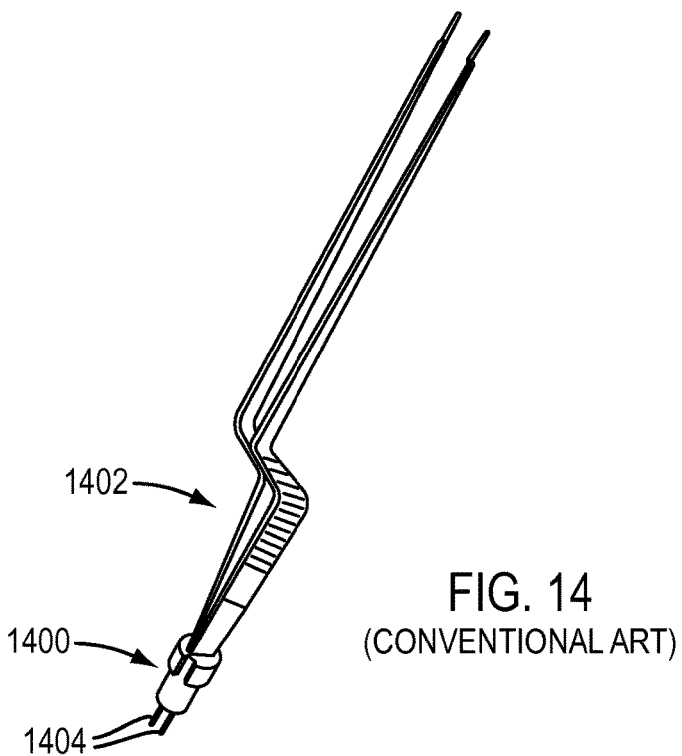
FIG. 14 is a perspective view of an electrosurgical instrument with a conventional connector interface.

In addition to the terminals 912, 922, the connector interfaces 910, 920 includes a data signal transmission terminal 914, 924 which, in the exemplary embodiments of FIGS. 9B and 9C, is a female connector, spaced vertically apart from the pair of flux transmission terminals 912, 922. The data signal transmission terminal 914, 924, as will be described in more detail below, provides identification data signals from, e.g., the electrosurgical instrument 1202 to a data signal processor, e.g., data interface module 208, 309. Specifically, the data signal transmission terminal 914, 924 is an interface of a data signal transmission line extending through the bipolar energy transmission cable 142. The bipolar energy transmission cable 142 interfaces with, for example, a flux delivery device, e.g., the bipolar electrosurgical instrument 1202, that is provided with identification data. The identification data is provided from the bipolar electrosurgical instrument 1202 through the data signal transmission line via the data signal transmission terminals 914, 924. The data signal transmission terminals 914, 924 are configured to engage with a corresponding data signal transmission terminal 1206 of the bipolar electrosurgical instrument 1202, shown in FIG. 12, in order to receive the identification data from the bipolar electrosurgical instrument 1202. The connector interfaces 910, 920 also are configured to engage with a conventional instrument connector interface, such as connector interface 1400 that does not include a data transmission capability, as shown in FIG. 14 for example. However, the data signal transmission terminals 914, 924 does not provide identification data from a conventional bipolar electrosurgical instrument, such as instrument 1402, as the conventional bipolar electrosurgical instrument does not transmit identification data or include a data signal transmission terminal at the connector interface 1400 but rather only includes the two bipolar energy terminals 1404.

Referring to FIG. 12, in an exemplary embodiment, the flux delivery instrument connector interface 1200 can be a recessed interface. The connector interface 1200 includes a pair of flux transmission terminals 1204, which are male connectors in the exemplary embodiment of FIG. 12, spaced apart from one another. The flux transmission terminals 1204 are configured to transmit flux from the bipolar energy transmission cable 142 to the bipolar electrosurgical instrument 1202. The connector interface 1200 additionally includes a data signal transmission terminal 1206, which is a male connector in the exemplary embodiment of FIG. 12, spaced apart from the pair of flux transmission terminals 1204. The data signal transmission terminal 1206 is in communication with an electronic chip at the bipolar electrosurgical instrument 1202. The data signal transmission terminal 1206 is configured to receive identification information of the bipolar electrosurgical instrument 1202 and transmit the identification information through the data transmission terminals 914, 924 of the bipolar energy transmission cable 142.

In the exemplary embodiment of FIG. 12, the recessed connector interface 1200 is designed to receive the connector interfaces 910, 920 shown in the embodiment of FIGS. 9B and 9C, the shape of the connector interfaces 910, 920 (e.g., having a larger, rounded shape around the flux transmission terminals 922 and a smaller, square shape at the data signal transmission terminal 924 corresponds with the shape of the recessed connector interface 1200. The corresponding shapes of portions of the connector interfaces 910, 920, and 1200 facilitate correct orientation of the connector interfaces 910, 920 of the bipolar energy transmission cable 142 in relation to the connector interface 1200 of the bipolar electrosurgical instrument 1202.

In accordance with another exemplary embodiment, the flux transmission conduit may be a monopolar energy transmission cable, such as monopolar energy transmission cable 144. FIG. 10A shows a first connector interface 1000 configured to connect with flux source connector interfaces 1130c, 1330d (shown in FIG. 11), which in an exemplary embodiment may be provided at the ESU 1102. FIGS. 10B and 10C show different configurations of another connector interface 1010, 1020 of the monopolar energy transmission cable 144 (shown in part in FIGS. 10B and 10C) configured to connect with a monopolar electrosurgical instrument 1302 at an instrument connector interface 1300 (the housing portion of the instrument that interfaces with an actuation interface assembly at the patient side cart being shown in FIG. 13).

As shown in FIG. 10A, the connector interface 1000 includes a single male flux transmission terminal 1002, configured to be placed in electrical energy contact with a connector interface at a flux supply source. The connector interface 1000 is configured to engage with a corresponding flux source connector interface to transmit flux from the flux supply source through the monopolar cable 144. In addition to the terminal 1002, the connector interface 1000 includes a data signal transmission terminal 1004, which may be, for example, an electrical contact ring, such as copper ring. The data signal transmission terminal 1004 transmits identification data from, e.g., the electrosurgical instrument 1302 (shown in FIG. 13) to a data signal processor, e.g., data interface module 208, 309, at the flux supply source. The data signal transmission terminal 1004 is an interface of a data signal transmission line extending through the monopolar energy transmission cable 144. When the monopolar energy transmission cable 144 interfaces with, for example, an electrosurgical instrument that is provided with identification data, the identification data is provided from the electrosurgical instrument through the data signal transmission line to the data signal transmission terminal 1004.

Referring back to FIG. 11, in an exemplary embodiment, flux supply source connector interfaces, such as monopolar connector interfaces 1130c, 1130d, are configured to connect to the monopolar energy transmission cable 144. The monopolar connector interfaces 1130c, 1130d each include a single female flux transmission terminal 1134 configured to receive the male terminal 1002 of FIG. 10C to enable the monopolar energy cable 144 to transmit electrical energy from the flux supply source 1102. The monopolar connector interfaces 1130c, 1130d also include a data signal transmission terminal 1138 spaced vertically from the female flux transmission terminal 1134. In the exemplary embodiment of FIG. 11, the data signal transmission terminal 1138 is an electrical finger or recess configured to mate with the data transmission terminal 1004 of the monopolar energy transmission cable connector interface 1000. In an exemplary embodiment, the data signal transmission terminal 1004 may be copper. The data signal transmission terminal 1138 enables the transmission of identification data from, e.g., the monopolar electrosurgical instrument 1302 (shown in FIG. 13) to a data signal processor, e.g., data interface module 208, 309. Specifically, the data signal transmission terminal 1138 is in data signal communication with the data signal processor.

When electrical energy is supplied through one of the monopolar connector interfaces 1130c, 1130d, the energy is transmitted from the flux generator via the female flux transmission terminal 1134 through the energy transmission line of the monopolar energy transmission cable 144. Also, identification data of the electrosurgical instrument 1302 is provided through the data signal transmission terminal 1004 and data transmission line of the conduit 144 to the corresponding flux supply source data signal transmission terminal 1138, which provides the identification data to a data signal processor, e.g., data interface module 208. The data signal processor may be provided at the ESU 1102.

In addition to being configured to be received at a flux supply source connector interface 1130c, 1130d of the present disclosure, the connector interface 1000 of the monopolar energy transmission cable 144 is configured to mate with a conventional flux source connector interface of, for example, a conventional ESU (not shown). In particular, the flux transmission terminals 1002 also are configured to mate with, and supply flux from, corresponding flux transmission terminals of a conventional flux supply source. Thus, users of the monopolar energy transmission cable 144 are not required to use an extra cable when converting between a flux source in accordance with exemplary embodiments of the present disclosure (e.g., the ESU 1102 including the flux source connector interface 1130c, 1130d) and a conventional flux source connector interface that does not include, for example, a monopolar connector interface with a data terminal.

Figure 15:
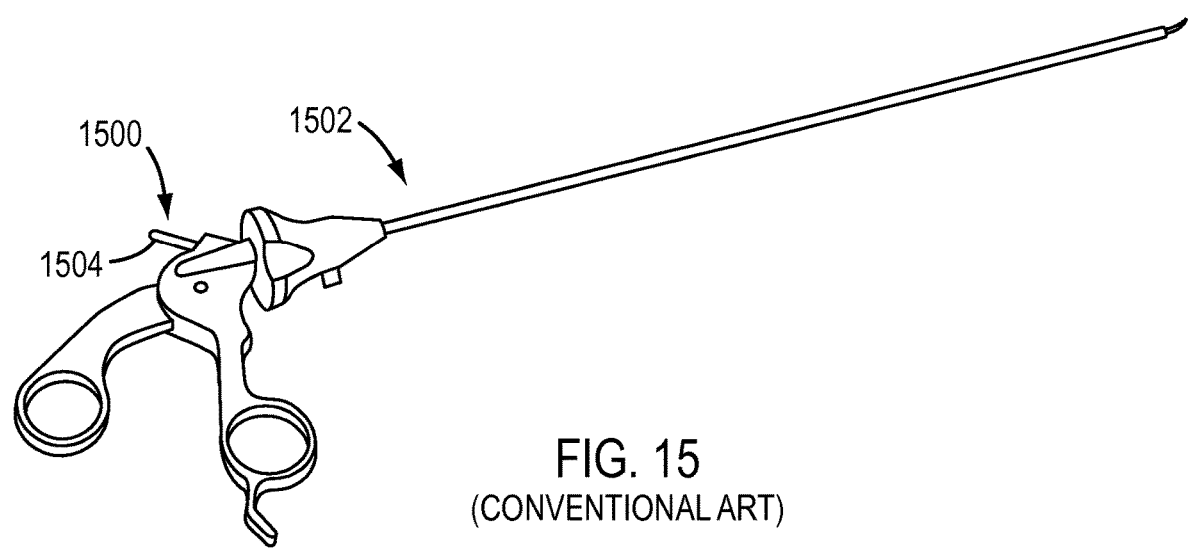
FIG. 15 is a perspective view of electrosurgical instrument with another conventional connector interface.

Turning now to FIGS. 10B and 10C, connector interfaces 1010, 1020 at the opposite end of connector interface 1000 of the monopolar energy transmission cable 144 are shown. The connector interfaces 1010, 1020 are configured to engage with a corresponding monopolar instrument connector interface, e.g., connector interface 1300 of a monopolar electrosurgical instrument 1302, shown in FIG. 13, and also with a conventional connector interface 1500 of a conventional monopolar instrument, as shown in FIG. 15. The connector interfaces 1010, 1020 include two flux transmission terminals 1012 and 1014, and 1022 and 1024, respectively, which are female connectors in the exemplary embodiment of FIGS. 10B and 10C, spaced apart from one another. Each of the flux transmission terminals 1012 and 1022 are configured to engage with a corresponding flux transmission terminal 1504, shown in FIG. 15, of a conventional instrument connector interface 1500 on a conventional monopolar electrosurgical instrument 1502 and provide electrical energy thereto.

The flux transmission terminals 1014, 1024 are sized smaller than the flux transmission terminals 1012, 1022, which correspond with conventional flux transmission terminals of a conventional instrument connector interface. The flux transmission terminals 1014, 1024 are configured to mate with a corresponding flux transmission terminal 1304 at the connector interface 1300 of the monopolar electrosurgical instrument 1302, as shown in an exemplary embodiment in FIG. 13. In an exemplary embodiment, the connector interface 1020 of FIG. 10C is configured to engage with the instrument connector interface 1300 shown in FIG. 13 to transmit flux to a monopolar electrosurgical instrument 1302 through the monopolar energy transmission cable 144.

In addition to the terminals 1012 and 1014, and 1022 and 1024, the connector interfaces 1010, 1020 include at least one data signal transmission terminal, 1016a and 1016b, or 1026. In the exemplary embodiments of FIGS. 10B and 10C, the at least one data signal transmission terminal 1016a, 1016b, or 1026 is a female connector, spaced apart from the flux transmission terminals 1012 and 1014, and 1022 and 1024, respectively. The at least one data signal transmission terminal 1016a, 1016b, or 1026, as will be described in more detail below, facilitates providing identification data from, e.g., the monopolar electrosurgical instrument 1202 to a data signal processor, e.g., data interface module 208. Specifically, the data signal transmission terminal 1016a, 1016b, or 1026 is an interface of a data signal transmission line extending along the monopolar energy transmission cable 144. When the monopolar energy transmission cable 144 interfaces with, for example, the monopolar electrosurgical instrument 1302 is provided with identification data, the identification data is provided from the monopolar electrosurgical instrument 1302 through the data signal transmission line via the data signal transmission terminal 1016a, 1016b, or 1026.

Figure 13:
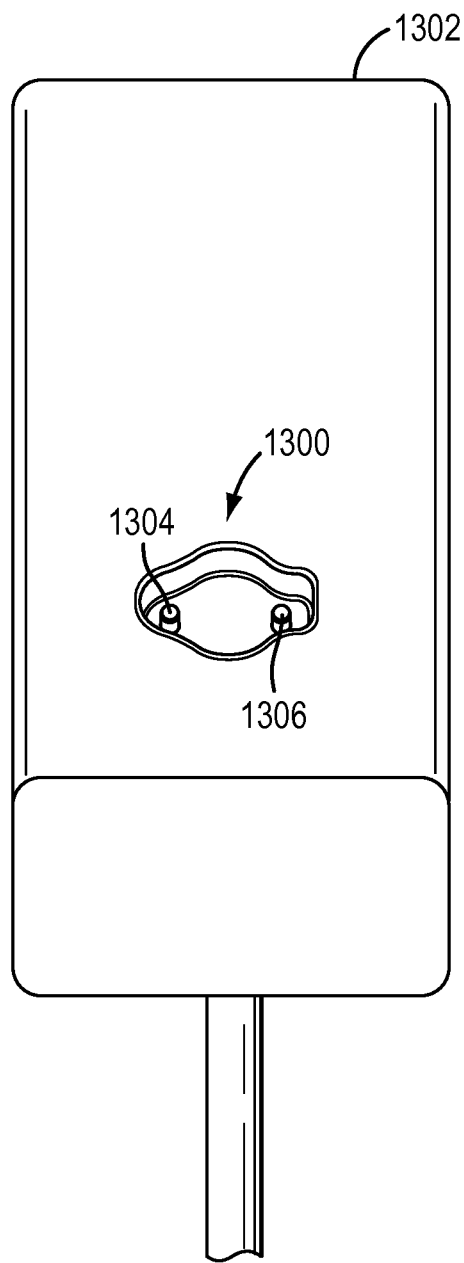
FIG. 13 is a top view of a connector interface of another electrosurgical instrument in accordance with one exemplary embodiment.

Referring to FIG. 13, in an exemplary embodiment, the flux delivery device connector interface 1300 is a recessed interface provided at a flux delivery device, e.g., monopolar electrosurgical instrument 1302. The connector interface 1300 includes the single flux transmission terminal 1304, which is a male connector in the exemplary embodiment of FIG. 13. The flux transmission terminal 1304 is configured to supply flux from a monopolar energy transmission cable 144 to the monopolar electrosurgical instrument 1302. The connector interface 1300 additionally includes the data signal transmission terminal 1306, which is a male connector in the exemplary embodiment of FIG. 13, spaced apart from the flux transmission terminal 1304. The data signal transmission terminal 1306 is in communication with an electronic chip at the monopolar electrosurgical instrument 1302. The data signal transmission terminal 1306 is configured to receive identification information of the monopolar electrosurgical instrument 1302 and transmit the identification information through the monopolar energy transmission cable 144.

The female flux transmission terminal 1014, 1024 is configured to mate with the male flux transmission terminal 1304. When electrical energy is supplied through the monopolar energy transmission cable 144, the energy is transmitted via the female flux transmission terminal 1014, 1024 through the energy transmission line within the monopolar energy transmission cable 144 to the male flux transmission terminal 1304 into the monopolar instrument 1302. The data signal transmission terminal(s) 1016a and 1016b, or 1026 of the monopolar energy transmission cable 144 is configured to mate with a corresponding data signal transmission terminal(s), e.g., data signal transmission terminal 1306 at the connector interface 1300 of the monopolar electrosurgical instrument 1302 (mating data signal transmission terminals for 1016a, 1016b not shown). Identification data of the electrosurgical instrument 1302 is provided through the data signal transmission terminal 1306 to the corresponding cable data signal transmission terminal 1016a and 1016b, or 1026 and transmitted through the data signal transmission line of the monopolar energy transmission cable 144.

In the exemplary embodiment of FIG. 13, the recessed connector interface 1300 is designed to receive the connector interface 1020 shown in the embodiment of FIG. 10C, where the shape of the connector interface 1020 (e.g., having a larger, rounded shape in the middle of the interface 1020, a smaller, rounded shape at one end of the interface 1020 and a smaller, square shape at another end of the interface 1020) of the monopolar energy transmission cable 144 corresponds with the shape of the recessed connector interface 1300. The corresponding shapes of portions of the connector interfaces 1020, 1300 facilitate correct orientation of the connector interface 1020 of the monopolar energy transmission cable 144 in relation to the connector interface 1300 of the monopolar electrosurgical instrument 1302.

One of ordinary skill in the art would recognize that any of the female terminals of the energy transmission cables, flux source connector interfaces, and instrument connector interfaces can be male terminals and vice versa. Those having ordinary skill in the art would appreciate other modifications that may be needed to the various connectors and receptacles in order to accommodate a modification of the terminal types.

In various exemplary embodiments, the flux transmission terminals and the data signal transmission terminals are sized and arranged such that they are able to mate only to corresponding respective flux transmission terminals and the data signal transmission terminals.

One of ordinary skill in the art would recognize that various other designs may be chosen for the connection of data signal transmission terminals between connector interfaces and flux transmission terminals between connector interfaces, as long as a mating or connecting relationship is formed between the appropriate terminals. Other design configurations in accordance with various exemplary embodiments can be selected, for example, by satisfying a set of design criteria set forth below in Table 1. Table 1 illustrates exemplary connecting and data transmission conditions of energy transmission cables (for both bipolar and monopolar energy) in accordance with exemplary embodiments of the present disclosure, to both conventional energy supply sources and energy supply sources of the present disclosure and to both conventional (e.g., handheld laparoscopic) electrosurgical instruments and electrosurgical instruments in accordance with the present disclosure (for both bipolar and monopolar instruments).

TABLE 1

| | Instrument (e.g., mono- or bi-polar energy) in accordance with present disclosure | Conventional (e.g., mono- or bi-polar energy) instrument | Energy supply source (e.g., mono- or bi-polar energy) in accordance with present disclosure | Conventional energy supply source (e.g., mono- or bi-polar energy) |
|---|---|---|---|---|
| Cable (e.g., mono- or bi-polar energy) in accordance with present disclosure | Connects; Identification data transmitted | Connects; no identification data transmitted | Connects; identification data received | Connects; no identification data received |
| Conventional (e.g., mono- or bi-polar energy) cable | Does not connect | Connects; no identification data transmitted | Connects; no identification data received | Connects; no identification data received |

In addition to the design criteria above, in accordance with various exemplary embodiments, the bipolar energy transmission cable 142 and the monopolar energy transmission cable 144 are designed so that the energy transmission cables 142, 144 are not interchangeable. In other words, the connector interfaces at each end of the respective cables 142, 144 are configured such that none of the connector interfaces 900, 910, or 920 at the ends of the bipolar energy transmission cable 142 can be connected with either the monopolar electrosurgical instrument connector interface 1300 or the monopolar flux supply source connector interfaces 1130c, 1130d, respectively. Similarly, none of the connector interfaces 1000, 1010, or 1020 at the ends of the monopolar energy transmission cable 144 can be connected with either the bipolar electrosurgical instrument connector interface 1200 or the bipolar flux supply source connector interfaces 1130a, 1130b, respectively. In this way, inadvertently routing monopolar energy to the bipolar electrosurgical instrument 1202 or bipolar energy to the monopolar electrosurgical instrument 1302 can be avoided. The overall connector interface shape, as well as the positioning and number of the flux transmission terminals and the data signal transmission terminals at both ends of each of the bipolar and monopolar energy transmission cables 142, 144 can be selected to uniquely differentiate the connector interfaces of the bipolar energy transmission cable 142 from the corresponding connector interfaces of the monopolar energy transmission cable 144. The connector interfaces 1200 and 1300 and the connector interfaces 1130a, 1130b and 1130c, 1130d also may have such unique and differentiating configurations so as to be able to mate only with the corresponding bipolar or monopolar cable.

Further, in accordance with various exemplary embodiments, the connector interfaces of the bipolar electrosurgical instrument 1202 or the monopolar electrosurgical instrument 1302 of the present disclosure are configured to prevent mating engagement with the connector interfaces of conventional bipolar and monopolar energy transmission cables (not shown and configured to engage with conventional bipolar or monopolar electrosurgical instruments). For example, referring to the exemplary embodiments of FIGS. 12 and 13, the shape and recessed configuration of the connector interfaces 1200, 1300 of the bipolar electrosurgical instrument 1202 and the monopolar electrosurgical instrument 1302, respectively, can be selected to prevent mating engagement of connector interfaces of conventional bipolar and monopolar energy transmission cables.

Moreover, in accordance with various exemplary embodiments, the configuration of the connector interfaces 910, 920, and 1010, 1020 of the bipolar energy transmission cable 142 and the monopolar energy transmission cable 144 are configured to mate to surgical instruments, such as electrosurgical instruments 1202, 1302 that are able to transmit data and provide the unique instrument identification information via the transmission cables 142, 144. However, the connector interfaces 910, 920, 1010, 1020 also are configured to mate to conventional electrosurgical instruments, such as those having conventional banana plug connector interface, that do not have data signal transmission capabilities via an energy transmission cable (e.g., via the energy connector interfaces of the conventional surgical instruments). In addition, the connector interfaces 900 and 1000 of the bipolar energy transmission cable 142 and the monopolar energy transmission cable 144 are configured to be mated to flux supply source connector interfaces 1130*a*, 1130*b*, and 1130*c*, 1130*d* that can receive and read data signals transmitted through the cables 142, 144. The connector interfaces 900, 1000 also are configured to mate to conventional flux source connector interfaces that include corresponding flux transmission terminals but do not include data signal terminals. This permits the use of energy transmission cables in accordance with the present disclosure with conventional flux supply sources (e.g., conventional electrosurgical generation units), for example, to transmit energy but that do not receive and read data signals through the energy transmission cable.

In accordance with various exemplary embodiments, the overall look and shape of the connector interfaces 910, 920, 1010, 1020 of the flux transmission conduits, e.g., cables 142, 144, are selected so as to be aesthetically appealing. The unique look and shape also allows users to readily recognize the transmission conduits, e.g., cables 142, 144, of the present disclosure from conventional flux transmission cables (e.g., electrosurgical energy transmission conduits) and from each other (e.g., bipolar versus monopolar). Similarly, the overall look and shape of the connector interfaces 1200, 1300 of the electrosurgical instruments 1202, 1302 also are selected so as to be aesthetically appealing and readily distinguishable from conventional instruments and each other. The unique shape also allows users to easily determine the appropriate flux transmission conduit that can be matingly engaged.

Exemplary embodiments, including the various operational methods described herein, can be implemented in computing hardware (computing apparatus) and/or software, such as (in a non-limiting example) any computer that can store, retrieve, process and/or output data and/or communicate with other computers. The results produced can be displayed on a display of the computing hardware. One or more programs/software comprising algorithms to affect the various responses and signal processing in accordance with various exemplary embodiments of the present disclosure can be implemented by a processor, such as data interface module, of or in conjunction with the control cart including core processor and may be recorded on computer-readable media including computer-readable recording and/or storage media. Examples of the computer-readable recording media include a magnetic recording apparatus, an optical disk, a magneto-optical disk, and/or a semiconductor memory (for example, RAM, ROM, etc.). Examples of the magnetic recording apparatus include a hard disk device (HDD), a flexible disk (FD), and a magnetic tape (MT). Examples of the optical disk include a DVD (Digital Versatile Disc), a DVD-RAM, a CD-ROM (Compact Disc-Read Only Memory), and a CD-R (Recordable)/RW.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are nonlimiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A method of supplying flux, the method comprising:
receiving first data at a control system in response to a remotely-controllable kinematic flux delivery structure being in an operationally coupled state with a flux supply pathway, the first data comprising information identifying the remotely-controllable kinematic flux delivery structure, the first data being transmitted from a first data source at the remotely-controllable kinematic flux delivery structure; and receiving second data at the control system in response to the remotely-controllable kinematic flux delivery structure being in an operationally coupled state with a kinematic support structure, the second data comprising information identifying the remotely-controllable kinematic flux delivery structure, the second data being transmitted from a second data source at the kinematic support structure;

wherein in response to receiving a flux delivery input command signal from an input device operationally coupled to the kinematic support structure, the control system:
compares the first data and the second data to verify the identifying information of the first data matches the identifying information of the second data and that the remotely-controllable kinematic flux delivery structure is in the operationally coupled state-with the kinematic support structure and that the remotely-controllable kinematic flux delivery structure is in the operationally coupled state with the flux supply pathway, and
sends a signal to supply flux from the flux supply pathway to the kinematic flux delivery structure upon verifying that the remotely-controllable kinematic flux delivery structure is in the operationally coupled state with the kinematic support structure and that the remotely-controllable kinematic flux delivery structure is in the operationally coupled state with the flux supply pathway.

2. The method of claim 1, wherein the kinematic support structure comprises an actuation interface assembly of a teleoperated surgical system patient side cart.

3. The method of claim 2, wherein receiving the second data comprises receiving unique identification data associated with the remotely-controllable kinematic flux delivery structure.

4. The method of claim 2, wherein:
the kinematic support structure further comprises a manipulator arm to which the actuation interface assembly is coupled; and
receiving the second data comprises receiving the second data from a data reader provided at the manipulator arm of the kinematic support structure.

5. The method of claim 1, wherein receiving the first data comprises receiving unique identification data associated with the remotely-controllable kinematic flux delivery structure, the unique identification data comprising data identifying a type of the remotely-controllable kinematic flux delivery structure.

6. The method of claim 1, wherein the kinematic support structure comprises a manipulator arm of a teleoperated surgical system patient side cart.

7. The method of claim 1, wherein the sending of the signal to supply flux comprises transmitting the signal via a router to provide flux from a flux generator port, the flux generator port being part of the flux supply pathway.

8. The method of claim 1, further comprising transmitting a second signal via the control system to output feedback identifying the operationally coupled state between the remotely-controllable kinematic flux delivery structure and the kinematic support structure, and the operationally coupled state between the remotely-controllable kinematic flux delivery structure and the flux supply pathway.

9. The method of claim 1, wherein the flux comprises at least one of electrosurgical energy, laser energy, ultrasound energy, radio frequency energy, nerve stimulation energy, an image stream, an audio stream, fluid, gas, and vacuum pressure.

10. The method of claim 1, wherein:
the first data source comprises an electronic circuit encoded with the information identifying the one of the remotely-controllable kinematic flux delivery structures, and
the second data source comprises a radio frequency identification device encoded with the information identifying the one of the remotely-controllable kinematic flux delivery structures.

11. A system for supplying flux, comprising:
a plurality of flux supply pathways;
a plurality of kinematic support structures;
a plurality of remotely-controllable kinematic flux delivery structures each operationally coupled to a corresponding differing one of the flux supply pathways and to a corresponding differing one of the kinematic support structures; and
a control system configured to:
receive first data comprising information identifying one of the remotely-controllable kinematic flux delivery structures in response to the one of the remotely-controllable kinematic flux delivery structures being in an operationally coupled state with one of the flux supply pathways, the first data being transmitted from a first data source at the one of the remotely controllable kinematic flux delivery structures, and
receive second data comprising information identifying the one of the remotely-controllable kinematic flux delivery structures in response to the one of the remotely-controllable kinematic flux delivery structures being in an operationally coupled state with the one of the kinematic support structures, the second data being transmitted from a second data source at the one of the kinematic support structures;
wherein the control system is configured to:
compare the first data and the second data to verify that the identifying information of the first data matches the identifying information of the second data and that the one of the remotely-controllable kinematic flux delivery structures is in the operationally coupled state with the one of the kinematic support structures and is in the operationally coupled state with the one of the flux supply pathways, and
send a signal to supply flux from the one of the flux supply pathways in response to receiving a flux delivery input command signal from an input device operationally coupled to the one of the kinematic support structures and in response to verifying the operationally coupled state between the one of the remotely-controllable kinematic flux delivery structures with the one of the kinematic support structures and between the one of the remotely-controllable kinematic flux delivery structures with the one of the flux supply pathways.

12. The system of claim 11, wherein:
each of the kinematic support structures comprises a manipulator arm of a teleoperated surgical system.

13. The system of claim 12, wherein each of the kinematic support structures further comprises an actuation interface assembly mounted to the associated manipulator arm, each of the remotely-controllable kinematic flux delivery structures being configured to be operationally coupled to a corresponding differing actuation interface assembly.

14. The system of claim 12, wherein each of the kinematic support structures further comprises a sterile drape connection mechanism located at the associated manipulator arm.

15. The system of claim 13, further comprising readable memory structures, each one of the readable memory structures being associated with a corresponding differing one of the remotely-controllable kinematic flux delivery structures, wherein the first data source is one of the readable memory structures provided at the one of the remotely-controllable kinematic flux delivery structures.

16. The system of claim 15, further comprising a plurality of data readers disposed to read the readable memory structures when the readable memory structures are located within a sufficient proximity of the data readers.

17. The system of claim 16, wherein the data readers are disposed to read a corresponding readable memory structure of a remotely-controllable flux delivery structure in an operationally coupled state of the remotely-controllable flux delivery structure with the associated actuation interface assembly.

18. The system of claim 11, further comprising a router, wherein the one of the flux supply pathways comprises one of a plurality of ports in flux communication with a flux generator, and wherein the control system is configured to transmit the signal to provide flux from the flux generator through the one of the plurality of ports via the router.

19. The system of claim 11, wherein the flux comprises at least one of electrosurgical energy, laser energy, ultrasound energy, radio frequency energy, nerve stimulation energy, an image stream, an audio stream, fluid, gas, and vacuum pressure.

20. The system of claim 11, wherein the control system is further configured to transmit a second signal to output feedback identifying that the one of the remotely-controllable kinematic flux delivery structures is in the operationally coupled state with the one of the kinematic support structures, and that the one of the remotely-controllable kinematic flux delivery structures is in the operationally coupled state with the one of the flux supply pathways.

21. The system of claim 11, wherein:
the first data source comprises an electronic circuit encoded with the information identifying the one of the remotely-controllable kinematic flux delivery structures, and
the second data source comprises a radio frequency identification device encoded with the information identifying the one of the remotely-controllable kinematic flux delivery structures.

\* \* \* \* \*